US008696602B2

(12) United States Patent
Semler et al.

(10) Patent No.: US 8,696,602 B2
(45) Date of Patent: Apr. 15, 2014

(54) METHOD OF DETERMINING BODY EXIT OF AN INGESTED CAPSULE

(75) Inventors: John R. Semler, Williamsville, NY (US); Kathleen H. Selover, East Concord, NY (US); Bemina L. Rohde, Cheektowaga, NY (US)

(73) Assignee: Given Imaging, Inc., Duluth, GA (US)

( * ) Notice: Subject to any disclaimer, the term of this patent is extended or adjusted under 35 U.S.C. 154(b) by 841 days.

(21) Appl. No.: 12/798,093

(22) Filed: Mar. 30, 2010

(65) Prior Publication Data

US 2010/0249645 A1 Sep. 30, 2010

Related U.S. Application Data

(60) Provisional application No. 61/211,492, filed on Mar. 31, 2009.

(51) Int. Cl.
 *A61B 5/117* (2006.01)
 *A61B 5/103* (2006.01)

(52) U.S. Cl.
 USPC .......................................... 600/593; 600/587

(58) Field of Classification Search
 USPC ................... 600/302, 561, 101–182, 582, 587
 See application file for complete search history.

(56) References Cited

U.S. PATENT DOCUMENTS

| 3,662,267 A | 5/1972 | Reed |
| 3,939,823 A | 2/1976 | Kaye |

(Continued)

FOREIGN PATENT DOCUMENTS

| DE | 344 0177 | 5/1986 |
| EP | 0 667 115 | 8/1995 |

(Continued)

OTHER PUBLICATIONS

DF Evans et al., Measurement of gastrointestinal pH profiles in normal ambulant human subjects, Gut, 1988, 29, 1035-1041.

(Continued)

*Primary Examiner* — Brian Szmal
*Assistant Examiner* — Huong Q. Nguyen
(74) *Attorney, Agent, or Firm* — Pearl Cohen Zedek Latzer Baratz LLP

(57) ABSTRACT

A method of determining body exit of an ingestible capsule comprising the steps of providing (40) an ingestible capsule (20) having a pressure sensor (23), having (41) a subject ingest the capsule, recording (42a) measurements from the pressure sensor as the capsule passes through at least an end portion of a gastrointestinal tract of the subject, transmitting (44) the measurements to a processor (31) outside of the gastrointestinal tract of the subject, identifying (47) an increasing pressure sequence (65) in the measurements between a selected start time (62) and a transmission end time (63), comparing (48) the sequence to a reference (66), and using the comparison to make a determination (52) regarding the capsule exiting the gastrointestinal tract of the subject. The increasing pressure sequence may be the longest increasing pressure sequence in the measurements. The reference may be a logarithmic regression of the measurements. The ingestible capsule may further comprise a temperature sensor (22) and the method may further comprising the steps of recording (42b) measurements from the temperature sensor as the capsule passes through the end portion of the gastrointestinal tract of the subject, transmitting (43) the measurements to the processor, analyzing (46) the temperature measurements for a substantial drop (68) in the temperature measurements, and using the analysis of the temperature measurements to make the determination regarding the capsule exiting the gastrointestinal tract of the subject.

69 Claims, 12 Drawing Sheets

(56) References Cited

U.S. PATENT DOCUMENTS

| | | |
|---|---|---|
| 4,219,821 A | 8/1980 | Selim |
| 4,278,077 A | 7/1981 | Mizumoto |
| 4,329,881 A | 5/1982 | Schloss |
| 4,854,328 A | 8/1989 | Pollack |
| 4,896,967 A | 1/1990 | Douglas-Hamilton et al. |
| 5,042,486 A | 8/1991 | Pfeiler et al. |
| 5,211,165 A | 5/1993 | Dumoulin et al. |
| 5,279,607 A | 1/1994 | Schentag et al. |
| 5,395,366 A | 3/1995 | D'Andrea et al. |
| 5,429,132 A | 7/1995 | Guy et al. |
| 5,515,853 A | 5/1996 | Smith et al. |
| 5,592,180 A | 1/1997 | Yokev et al. |
| 5,604,531 A | 2/1997 | Iddan et al. |
| 5,697,377 A | 12/1997 | Wittkampf |
| 5,736,958 A | 4/1998 | Turpin |
| 5,802,135 A | 9/1998 | Wohlrab |
| 5,913,820 A | 6/1999 | Bladen et al. |
| 5,984,860 A | 11/1999 | Shan |
| 5,993,378 A | 11/1999 | Lemelson |
| 6,172,640 B1 | 1/2001 | Durst et al. |
| 6,188,355 B1 | 2/2001 | Gilboa |
| 6,190,395 B1 | 2/2001 | Williams |
| 6,233,476 B1 | 5/2001 | Strommer et al. |
| 6,240,312 B1 | 5/2001 | Alfano et al. |
| 6,419,626 B1 | 7/2002 | Yoon |
| 6,453,190 B1 | 9/2002 | Acker et al. |
| 6,580,938 B1 | 6/2003 | Acker |
| 6,632,216 B2 | 10/2003 | Houzego et al. |
| 6,690,963 B2 | 2/2004 | Ben-Haim et al. |
| 6,904,308 B2 | 6/2005 | Frisch et al. |
| 6,929,636 B1 | 8/2005 | von Alten et al. |
| 6,934,573 B1 | 8/2005 | Glukhovsky et al. |
| 6,939,290 B2 | 9/2005 | Iddan |
| 6,950,690 B1 | 9/2005 | Meron et al. |
| 6,951,536 B2 | 10/2005 | Yokoi et al. |
| 7,009,634 B2 | 3/2006 | Iddan et al. |
| 7,104,952 B2 | 9/2006 | Iddan et al. |
| 7,118,529 B2 | 10/2006 | Iddan et al. |
| 7,144,366 B2 | 12/2006 | Takizawa et al. |
| 7,200,253 B2 | 4/2007 | Glukhovsky |
| 7,319,781 B2 | 1/2008 | Chen et al. |
| 7,354,397 B2 | 4/2008 | Fujita et al. |
| 7,585,283 B2 | 9/2009 | Kraizer et al. |
| 7,708,705 B2 | 5/2010 | Iddan |
| 7,844,317 B2 | 11/2010 | Salla et al. |
| 7,922,653 B2 | 4/2011 | Homan |
| 8,406,490 B2 | 3/2013 | Gat |
| 2001/0035902 A1 | 11/2001 | Iddan et al. |
| 2001/0051766 A1 | 12/2001 | Gazdzinski |
| 2002/0099310 A1 | 7/2002 | Kimchy et al. |
| 2002/0103417 A1 | 8/2002 | Gazdzinski |
| 2002/0111544 A1 | 8/2002 | Iddan |
| 2002/0162399 A1 | 11/2002 | Esashi |
| 2002/0198470 A1 | 12/2002 | Imran et al. |
| 2003/0013370 A1 | 1/2003 | Glukhovsky |
| 2003/0065250 A1 | 4/2003 | Chiel |
| 2003/0143182 A1 | 7/2003 | Vasconcellos et al. |
| 2003/0167000 A1 | 9/2003 | Mullick et al. |
| 2003/0191430 A1 | 10/2003 | D'Andrea et al. |
| 2003/0195415 A1 | 10/2003 | Iddan |
| 2003/0213495 A1 | 11/2003 | Fujita et al. |
| 2003/0214580 A1 | 11/2003 | Iddan |
| 2004/0087832 A1 | 5/2004 | Glukhovsky et al. |
| 2004/0106849 A1 | 6/2004 | Cho |
| 2004/0162501 A1 | 8/2004 | Imran |
| 2004/0171915 A1 | 9/2004 | Glukhovsky et al. |
| 2004/0176685 A1 | 9/2004 | Takizawa et al. |
| 2005/0261551 A1 | 11/2005 | Couvillon, Jr. |
| 2006/0120484 A1 | 6/2006 | Matsumoto et al. |
| 2006/0146739 A1 | 7/2006 | Matsumoto et al. |
| 2006/0149126 A1 | 7/2006 | Ertas et al. |
| 2006/0183993 A1 | 8/2006 | Horn |
| 2007/0129703 A1 | 6/2007 | Andrea et al. |
| 2007/0225560 A1 | 9/2007 | Avni et al. |
| 2008/0033257 A1 | 2/2008 | Yokoi et al. |
| 2008/0039687 A1 | 2/2008 | Shimizu et al. |
| 2008/0064938 A1 | 3/2008 | Semler et al. |
| 2008/0177136 A1 | 7/2008 | Wang |
| 2008/0255635 A1 | 10/2008 | Bettesh et al. |
| 2009/0005642 A1 | 1/2009 | Shigemori et al. |
| 2009/0274347 A1* | 11/2009 | Gat et al. ............... 382/128 |
| 2009/0318783 A1* | 12/2009 | Rohde et al. ............ 600/302 |
| 2010/0280348 A1* | 11/2010 | Wenzel et al. ........... 600/365 |

FOREIGN PATENT DOCUMENTS

| | | |
|---|---|---|
| EP | 1867280 | 12/2007 |
| EP | 1 872 710 | 1/2008 |
| JP | 57-45833 | 5/1982 |
| JP | 02-31738 | 2/1990 |
| JP | 4-109927 | 4/1992 |
| JP | 1992-144533 | 5/1992 |
| JP | 6154191 | 6/1994 |
| JP | 6285044 | 10/1994 |
| JP | 07-111985 | 5/1995 |
| JP | 7111985 | 5/1995 |
| JP | 7255692 | 10/1995 |
| JP | 2001046358 | 2/2001 |
| JP | 2001231186 | 8/2001 |
| JP | 2001231187 | 8/2001 |
| KR | 2002/089669 | 11/2002 |
| WO | WO 98/11816 | 3/1998 |
| WO | WO 98/29030 | 7/1998 |
| WO | WO9837926 | 9/1998 |
| WO | WO 99/32028 | 7/1999 |
| WO | WO 00/10456 | 3/2000 |
| WO | WO 01/06917 | 2/2001 |
| WO | WO 01/08548 | 2/2001 |
| WO | WO 01/50941 | 7/2001 |
| WO | WO 01/65995 | 9/2001 |
| WO | WO 03/021529 | 3/2003 |
| WO | WO 03/028224 | 4/2003 |
| WO | WO 03/090618 | 11/2003 |
| WO | WO03096889 | 11/2003 |
| WO | WO 2004/036803 | 4/2004 |
| WO | WO 2006/059331 | 6/2006 |
| WO | WO 2006-077529 | 7/2006 |
| WO | WO 2006/077529 | 7/2006 |
| WO | WO 2007/026891 | 3/2007 |
| WO | WO 2007/066288 | 6/2007 |

OTHER PUBLICATIONS

Z. Lin and J.D.Z. Chen, Comparison of three running spectral analysis methods for electrograstrographic signals, Med. & Biol., Eng. & Comput., 1995, 33, 596-604.

International Search Report of International Application PCT/IL03/00559, mailed Dec. 29, 2003.

Park, et al., "A Technique for Position Detection of Miniatured Wireless Telemetry Module in the Human Body", Proceedings of the 32nd ISR (International Symposium on Robotics), Apr. 19-21 2001,pp. 1888-1892.

Park, et al., "Design of Bi-directional and Multi-Channel Miniaturized Telemetry Module for Wireless Endoscopy", 2nd Annual International IEEE-EMBS Special Topic Conference on Microtechnologies in Medicine &Biology, May 2-4, 2002, Madison, Wisconsin USA pp. 273-276.

Park, et al., "Design of Miniaturized Telemetry Module for Bi-Directional Wireless Endoscopy", May 2-4, 2002.

Park, et al., "A Technique for Localization of Biomedical Telemetry Sensor in Human Body", Proceedings of the International Sensor Conference 2001, Seoul, Korea.

Nam, et al., "A method for Position Detection of the wireless capsule endoscopes Module Using the Solution of Nonlinear Simultaneous Equations", Sensors Conference 2002, p. 377.

Nam, et al., "A method for Position Detection of Miniaturized Telemetry Module Using the Solution of Nonlinear Simultaneous Equations", 2002.

"Localization of a wireless capsule endoscope in the GI Tract", Gastrointestinal Endoscopy 2001;53:AB126.

www.ibcdigital.com/ibc/animation_galleries/visualization.

(56) References Cited

OTHER PUBLICATIONS

European Search Report for European Application No. 09 00 4718 dated Jun. 16, 2009.
Office Action for European Patent Application No. 09004718.4 mailed Jun. 18, 2012.
European Search Report for European Application No. 08 154 317 dated Aug. 4, 2008.
European Office Action for European Application No. 08 154 317 dated Mar. 31, 2006.
Office Action for U.S. Appl. No. 12/059,420 mailed Jun. 8, 2011.
Final Office Action for U.S. Appl. No. 12/059,420 mailed Dec. 8, 2011.
Office Action for U.S. Appl. No. 12/059,420 mailed Mar. 1, 2012.
Notice of Allowance for U.S. Appl. No. 12/059,420 mailed Aug. 21, 2012.
Office Action for U.S. Appl. No. 10/519,918 mailed Oct. 20, 2006.
Final Office Action for U.S. Appl. No. 10/519,918 mailed May 7, 2007.
Office Action for U.S. Appl. No. 10/519,918 mailed Jan. 4, 2008.
Restriction Requirement for U.S. Appl. No. 10/519,918 mailed Jun. 26, 2008.
Final Office Action for U.S. Appl. No. 10/519,918 mailed Nov. 28, 2008.
Office Action for U.S. Appl. No. 10/519,918 mailed Jun. 9, 2009.
Notice of Allowance for U.S. Appl. No. 10/519,918 mailed Mar. 2, 2010.

* cited by examiner

METHOD OF DETERMINING BODY EXIT OF AN INGESTED CAPSULE

CROSS-REFERENCE TO RELATED APPLICATIONS

This application claims the benefit of U.S. Provisional Patent Application No. 61/211,492, filed Mar. 31, 2009. The entire content of such application is incorporated by reference herein.

TECHNICAL FIELD

The present invention relates generally to ingestible capsules and, more particularly, to a process for determining the body exit of an ingested capsule.

BACKGROUND ART

Ingestible capsules are well-known in the prior art. Such capsules are generally small pill-like devices that can be ingested or swallowed by a patient. It is known that such capsules may include one or more sensors for determining physiological parameters of the gastrointestinal tract, such as sensors for detecting temperature, pH and pressure.

A number of methods of determining location of an ingestible capsule are known in the prior art. For example, it is known that signal strength or signal triangulation may be used to attempt to determine the location of an ingested capsule. However, the use of an RF signal has a number of disadvantages, including that it generally requires multiple antennas, various tissues may impact the signal differently, and patient movement may skew the results. It is also known that accelerometers may be used to attempt to determine location, but such methods also have disadvantages, such as drift, non-linear progression and rotational inaccuracy.

It is also known that certain physiological parameters may be associated with regions of the gastrointestinal tract. For example, a 1988 article entitled "Measurement of Gastrointestinal pH Profiles in Normal Ambulant Human Subjects" discloses pH measurements recorded by a capsule passing through the gastrointestinal tract. It is known that pH has been correlated with transitions from the stomach to the small bowel (gastric emptying) and from the distal small bowel to the colon (ileo-caecal) junction.

DISCLOSURE OF THE INVENTION

With parenthetical reference to corresponding parts, portions or surfaces of the disclosed embodiment, merely for the purposes of illustration and not by way of limitation, the present invention provides an improved method of determining body exit of an ingestible capsule comprising the steps of providing (40) an ingestible capsule (20) having a pressure sensor (23), having (41) a subject ingest the capsule, recording (42a) measurements from the pressure sensor as the capsule passes through at least an end portion of a gastrointestinal tract of the subject, transmitting (44) the measurements to a processor (31) outside of the gastrointestinal tract of the subject, identifying (47) an increasing pressure sequence (65) in the measurements between a selected start time (62) and a transmission end time (63), comparing (48) the sequence to a reference (66), and using the comparison to make a determination (52) regarding the capsule exiting the gastrointestinal tract of the subject.

The increasing pressure sequence may be the longest increasing pressure sequence in the measurements. The reference may be a logarithmic regression of the measurements. The ingestible capsule may further comprise a temperature sensor (22) and the method may further comprising the steps of recording (42b) measurements from the temperature sensor as the capsule passes through the end portion of the gastrointestinal tract of the subject, transmitting (43) the measurements to the processor, analyzing (46) the temperature measurements for a substantial drop (68) in the temperature measurements, and using the analysis of the temperature measurements to make the determination regarding the capsule exiting the gastrointestinal tract of the subject. The method may further comprise the step of conditioning (53) the measurements between the selected start time and the transmission end time to provide terminating pressure data as a function of time (64), and wherein the increasing pressure sequence is identified in the terminating pressure data. The step of conditioning the pressure measurements may comprise the steps of screening the measurements to verify that they are valid, converting the measurements to units of pressure, and scaling the units of pressure such that ambient atmospheric pressure is set at a zero baseline. The step of transmitting the measurements to a processor may comprise the steps of transmitting the measurements from the capsule to a receiver (17) outside of the gastrointestinal tract of the subject, and downloading the measurements from the receiver to the processor. The selected start time may be about one hour prior to the transmission end time. The method may further comprise the step of providing a positive determination (54) regarding the capsule exiting the gastrointestinal tract of the subject when the comparison indicates a match. A standard correlation coefficient of about 0.8 or greater may indicate that the comparison is a match and a standard correlation coefficient of less than about 0.8 may indicate that the comparison is not a match. The method may further comprise the step of providing a positive determination regarding the capsule exiting the gastrointestinal tract of the subject when the comparison indicates a match or there is the substantial drop in the temperature measurements. The method may further comprise the step of providing a negative determination (55) regarding the capsule exiting the gastrointestinal tract when the comparison indicates not a match and there is not the substantial drop in the temperature measurements. The ingestible capsule may further comprise a power source (21) adapted to provide current to an electrical circuit housed in the capsule and the method may further comprise the steps of measuring (43) voltage for the circuit as the capsule passes through the gastrointestinal tract of the subject, transmitting (44c) the voltage measurements to the processor, analyzing (45) the voltage measurements for a low voltage condition and using the analysis of the voltage measurements to make the determination regarding the capsule exiting the gastrointestinal tract of the subject. The method may further comprise the step of providing a negative determination regarding the capsule exiting the gastrointestinal tract when the low voltage condition is indicated, and the low voltage condition may comprise a voltage measurement of less than about 2.5 volts or the low voltage condition may comprise a series of decreasing voltage measurements over a time period. The method may further comprise the step of displaying (56) the determination regarding the capsule exiting the gastrointestinal tract of the subject on a display (32).

In another aspect the invention provides a method of determining body exit of an ingestible capsule comprising the steps of providing an ingestible capsule having a pressure sensor, a temperature sensor and a power source adapted to provide current to an electrical circuit housed in the capsule, having a subject ingest the capsule, recording measurements from the pressure sensor and the temperature sensor as the capsule passes through at least an end portion of a gastrointestinal tract of the subject, measuring voltage for the circuit as the capsule passes through the gastrointestinal tract of the subject, transmitting the measurements to a processor outside of the gastrointestinal tract of the subject, analyzing the voltage measurements for a low voltage condition, analyzing the temperature measurements for a substantial drop in the temperature measurements, identifying a longest consecutive increasing pressure sequence in the pressure measurements from a selected start time to a transmission end time to provide terminating pressure data as a function of time, comparing the pressure sequence to a reference, and making a determination regarding the capsule exiting the gastrointestinal tract of the subject as a function of the comparison, the analysis of the temperature measurements, and the analysis of the voltage measurements.

The step of making a determination regarding the capsule exiting the gastrointestinal tract of the subject may comprise the steps of determining if the comparison is a match, determining if there is a corresponding substantial drop in the temperature measurements and determining if there is a low voltage condition. The method may further comprise the step of providing a positive determination regarding the capsule exiting the gastrointestinal tract when the comparison is a match, there is the corresponding substantial drop in the temperature measurements, and there is not the low voltage condition. The method may further comprise the step of providing a negative determination regarding the capsule exiting the gastrointestinal tract when the comparison is not a match, there is not the corresponding substantial drop in the temperature measurements, or there is the low voltage condition.

In another aspect, the invention provides a method of determining body exit of an ingestible capsule comprising the steps of providing an ingestible capsule having a pressure sensor and a temperature sensor, having a subject ingest the capsule, recording measurements from the pressure sensor and the temperature sensor as the capsule passes through at least an end portion of a gastrointestinal tract of the subject, transmitting the measurements to a processor outside of the gastrointestinal tract of the subject, analyzing the temperature measurements for a decrease in temperature, providing (49) a terminating data (69) set for the pressure and temperature measurements between the first decrease in temperature (73) and the transmission end time (63), analyzing (51) the terminating data set to determine a relationship between the pressure and the temperature measurements, comparing (57) the relationship to a reference (71), and using the comparison to make a determination regarding the capsule exiting the gastrointestinal tract of the subject.

The reference may comprise a thermal coefficient of sensitivity for the pressure sensor in pressure units per units of temperature, and the relationship may comprise the slope of a linear regression of the terminating data set. The step of analyzing the terminating data set may comprise the steps of organizing the pressure and temperature measurements into data pairs (69), performing a linear regression with respect to the data pairs to provide a best fit line (70), and determining the slope of the best fit line. The step of comparing the relationship to a reference may comprise comparing the slope to the thermal coefficient of sensitivity for the pressure sensor. The method may further comprise the step of providing a positive determination (54) regarding the capsule exiting the gastrointestinal tract of the subject when the comparison is positive. The method may further comprise the step of conditioning the pressure measurements prior to the step of providing a terminating data set for the pressure and temperature measurements between the decrease in temperature and the transmission end time, and the step of conditioning the pressure measurements may comprise the steps of screening the pressure measurements to verify that they are valid, converting the pressure measurements to units of pressure, and scaling the units of pressure such that ambient atmospheric pressure is set at a zero baseline. The step of transmitting the measurements to a processor may comprise the steps of transmitting the measurements from the capsule to a receiver outside of the gastrointestinal tract of the subject, and downloading the measurements from the receiver to the processor. The selected start time may be about one hour prior to the transmission end time. The ingestible capsule may further comprise a power source adapted to provide current to an electrical circuit housed in the capsule and the method may further comprise the steps of measuring voltage for the circuit as the capsule passes through the gastrointestinal tract of the subject, transmitting the voltage measurements to the processor, analyzing the voltage measurements for a low voltage condition and using the analysis of the voltage measurements to make the determination regarding the capsule exiting the gastrointestinal tract of the subject. The low voltage condition may comprise a series of decreasing voltage measurements over a time period. The method may further comprise the steps of determining (50) a correlation value between temperature and pressure data in the terminating data set, and using the correlation value to make a determination regarding the capsule exiting the gastrointestinal tract of the subject, and the step of determining a correlation value between temperature and pressure data in the terminating data set may comprise the step of performing a linear regression with respect to the data set. The correlation value may be an R-squared correlation coefficient for the linear regression. A correlation coefficient of about 0.9 or greater may indicate that the determination is positive and a correlation coefficient of less than about 0.9 may indicate that the determination is not positive.

In another aspect, the invention provides a method of determining body exit of an ingestible capsule comprising the steps of providing an ingestible capsule having a pressure sensor and a temperature sensor, having a subject ingest the capsule, recording measurements from the pressure sensor and the temperature sensor as the capsule passes through at least an end portion of a gastrointestinal tract of the subject, transmitting the measurements to a processor outside of the gastrointestinal tract of the subject, analyzing the temperature measurements for a decrease in temperature, providing a terminating data set for the pressure and temperature measurements between the decrease in temperature and the transmission end time, determining (50) a correlation value between temperature and pressure data in the terminating data set, and using the correlation value to make a determination regarding the capsule exiting the gastrointestinal tract of the subject.

The step of determining a correlation value between temperature and pressure data in the terminating data set may comprise the step of performing a linear regression (70) with respect to the data set. The correlation value may be an R-squared correlation coefficient for the linear regression. A correlation coefficient of about 0.9 or greater may indicate that the determination is positive and a correlation coefficient of less than about 0.9 may indicate that the determination is not positive.

In another aspect, the invention provides a computer-readable medium having computer-executable instructions for performing a method comprising receiving pressure measurements recorded by a pressure sensor on an ingestible capsule ingested by a subject, identifying an increasing pressure sequence in the measurements between a selected start time and a transmission end time, comparing the sequence to a reference, and using the comparison to make a determination regarding the capsule exiting the gastrointestinal tract of the subject.

The increasing pressure sequence may be the longest increasing pressure sequence in the measurements. The reference may be a logarithmic regression of the measurements. The medium may further comprise receiving temperature measurements recorded by a temperature sensor on the ingestible capsule, analyzing the temperature measurements for a substantial drop in the temperature measurements, and using the analysis of the temperature measurements to make the determination regarding the capsule exiting the gastrointestinal tract of the subject. The medium may further comprise conditioning the measurements between the selected start time and the transmission end time to provide terminating pressure data as a function of time, and wherein the increasing pressure sequence is identified in the terminating pressure data, and conditioning the measurements may comprise screening the measurements to verify that they are valid, converting the measurements to units of pressure, and scaling the units of pressure such that ambient atmospheric pressure is set at a zero baseline. The selected start time may be about one hour prior to the transmission end time. The medium my further comprise the steps of receiving voltage measurements recorded by the ingestible capsule, analyzing the voltage measurements for a low voltage condition, and using the analysis of the voltage measurements to make the determination regarding the capsule exiting the gastrointestinal tract of the subject.

In another aspect, the invention provides a system for identifying the body exit of an ingestible capsule from a gastrointestinal tract comprising an ingestible capsule having a pressure sensor adapted to record pressure data as a function of time as the capsule passes through at least a portion of a subject's gastrointestinal tract, a receiver adapted to received the data when transmitted from the capsule, a processor adapted to communicate with the receiver, a display in communication with the processor, the processor programmed to receive pressure measurements recorded by the pressure sensor, identify an increasing pressure sequence in the measurements between a selected start time and a transmission end time, compare the sequence to a reference, and use the comparison to make a determination regarding the capsule exiting the gastrointestinal tract of the subject.

The increasing pressure sequence may be the longest increasing pressure sequence in the measurements, and the reference may be a logarithmic regression of the measurements. The ingestible capsule may further comprise a temperature sensor adapted to record temperature data as a function of time as the capsule passes through at least a portion of a subject's gastrointestinal tract, and the processor may be further programmed to receive temperature measurements recorded by the temperature sensor, analyze the temperature measurements for a substantial drop in the temperature measurements, and use the analysis of the temperature measurements to make the determination regarding the capsule exiting the gastrointestinal tract of the subject. The processor may be further programmed to condition the measurements between the selected start time and the transmission end time to provide terminating pressure data as a function of time, and wherein the increasing pressure sequence is identified in the terminating pressure data. Conditioning the measurements may comprise screening the measurements to verify that they are valid, converting the measurements to units of pressure, scaling the units of pressure such that ambient atmospheric pressure is set at a zero baseline. The selected start time may be about one hour prior to the transmission end time. The processor may be further programmed to receive voltage measurements recorded by the ingestible capsule, analyze the voltage measurements for a low voltage condition, and use the analysis of the voltage measurements to make the determination regarding the capsule exiting the gastrointestinal tract of the subject.

In another aspect, the invention provides a computer-readable medium having computer-executable instructions for performing a method comprising receiving pressure measurements recorded by a pressure sensor and temperature measurements recorded by a temperature sensor on an ingestible capsule ingested by a subject, analyzing the temperature measurements for a decrease in temperature, providing a terminating data set for the pressure and temperature measurements between the decrease in temperature and a transmission end time, analyzing the terminating data set to determine a relationship between the pressure and the temperature measurements, comparing the relationship to a reference, and using the comparison to make a determination regarding the capsule exiting the gastrointestinal tract of the subject. The reference may comprise a thermal coefficient of sensitivity for the pressure sensor in pressure units per units of temperature. The relationship may comprise the slope of a linear regression of the terminating data set. Analyzing the terminating data set may comprise organizing the pressure and temperature measurements into data pairs, performing a linear regression with respect to the data pairs to provide a best fit line, and determining the slope of the best fit line. Comparing the relationship to a reference may comprise comparing the slope to the thermal coefficient of sensitivity for the pressure sensor. The medium may further comprise determining a correlation value between temperature and pressure data in the terminating data set, and using the correlation value to make a determination regarding the capsule exiting the gastrointestinal tract of the subject. Determining a correlation value between temperature and pressure data in the terminating data set may comprise performing a linear regression with respect to the data set. The correlation value may be an R-squared correlation coefficient for the linear regression. A correlation coefficient of about 0.9 or greater may indicate that the determination is positive and a correlation coefficient of less than about 0.9 may indicate that the determination is not positive.

In another aspect, the invention provides a computer-readable medium having computer-executable instructions for performing a method comprising receiving pressure measurements recorded by a pressure sensor and temperature measurements recorded by a temperature sensor on an ingestible capsule ingested by a subject, analyzing the temperature measurements for a decrease in temperature, providing a terminating data set for the pressure and temperature measurements between the decrease in temperature and a transmission end time, determining a correlation value between temperature and pressure data in the terminating data set, and using the correlation value to make a determination regarding the capsule exiting the gastrointestinal tract of the subject.

Determining a correlation value between temperature and pressure data in the terminating data set may comprise performing a linear regression with respect to the data set, and the correlation value may be an R-squared correlation coefficient for the linear regression. A correlation coefficient of about 0.9 or greater may indicate that the determination is positive and a correlation coefficient of less than about 0.9 may indicate that the determination is not positive.

Accordingly, the general object is to provide a method for determining the body exit time of an ingestible capsule.

Another object is to provide a method for confirming the expulsion time of a capsule from the gastrointestinal tract of a subject based on pressure and temperature patterns.

These and other objects and advantages will become apparent from the foregoing and ongoing written specification, the drawings, and the claims.

DESCRIPTION OF PREFERRED EMBODIMENTS

Figure 1A:
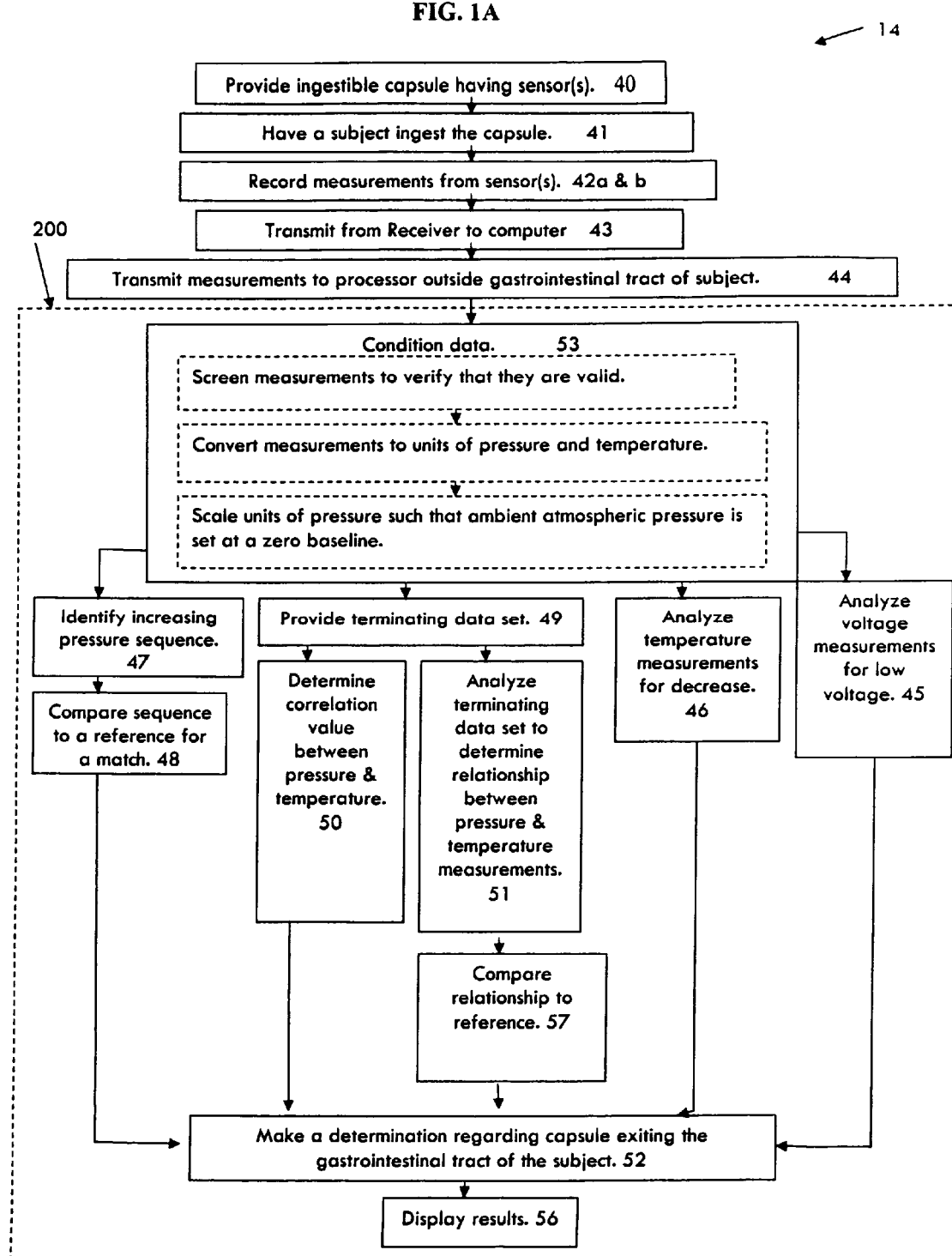
FIG. 1A is a flow chart of an embodiment of the method.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 10:
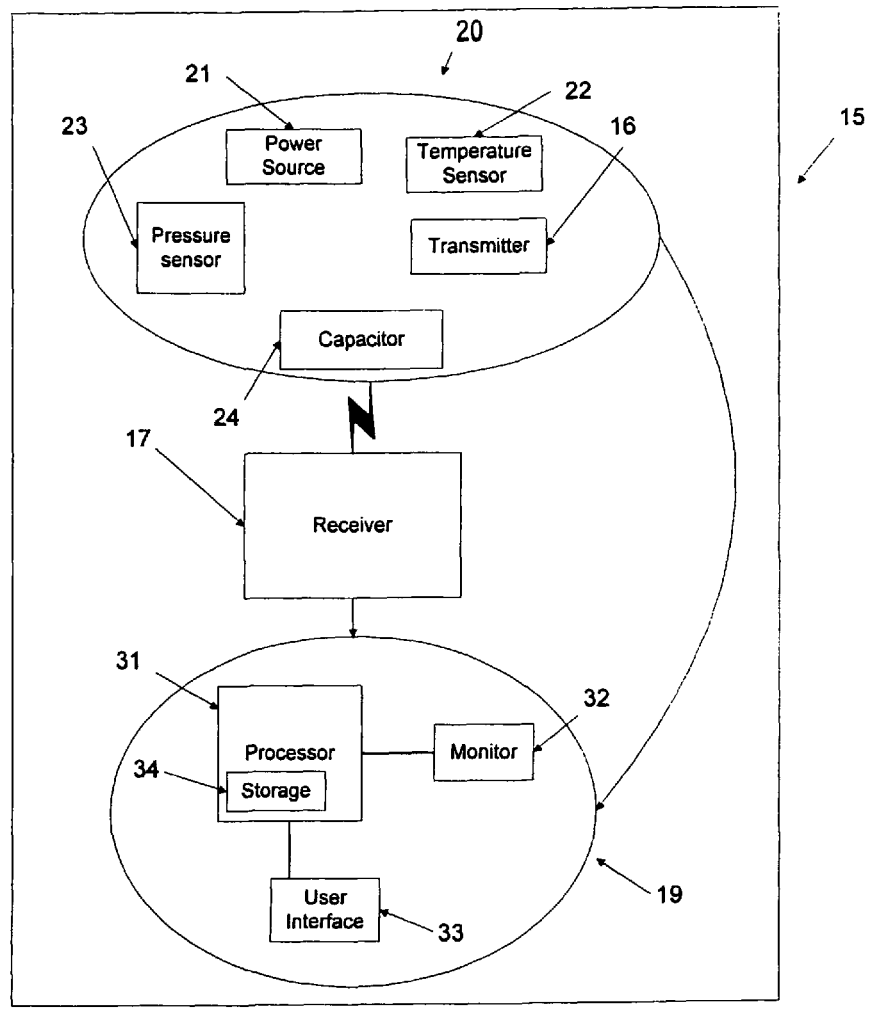
FIG. 10 is a schematic of an embodiment of the capsule system.

Referring now to the drawings and, more particularly, to FIG. 1 thereof, this invention provides a new method for determining the body exit time of an ingested capsule from the gastrointestinal tract of a subject, of which a first embodiment is generally indicated at 14. As shown in FIG. 10, process 14 is performed using capsule system 15, which generally includes ingestible capsule 20, receiver 17, and computer workstation 19. Capsule 20 includes pressure sensor assembly 23 and temperature sensor 22 for taking measurements of pressure and temperature, respectively, of a subject's gastrointestinal tract, capacitor 24, power source 21, and transmitter 16 for transmitting the measurement data. Receiver 17 is configured to receive signals sent from transmitter 16. Computer workstation 19 includes processor 31 and is programmed to process measurements from pressure sensor 23, temperature sensor 22, and capacitor 24 to determine capsule 20's body exit time (BET).

Figure 11:
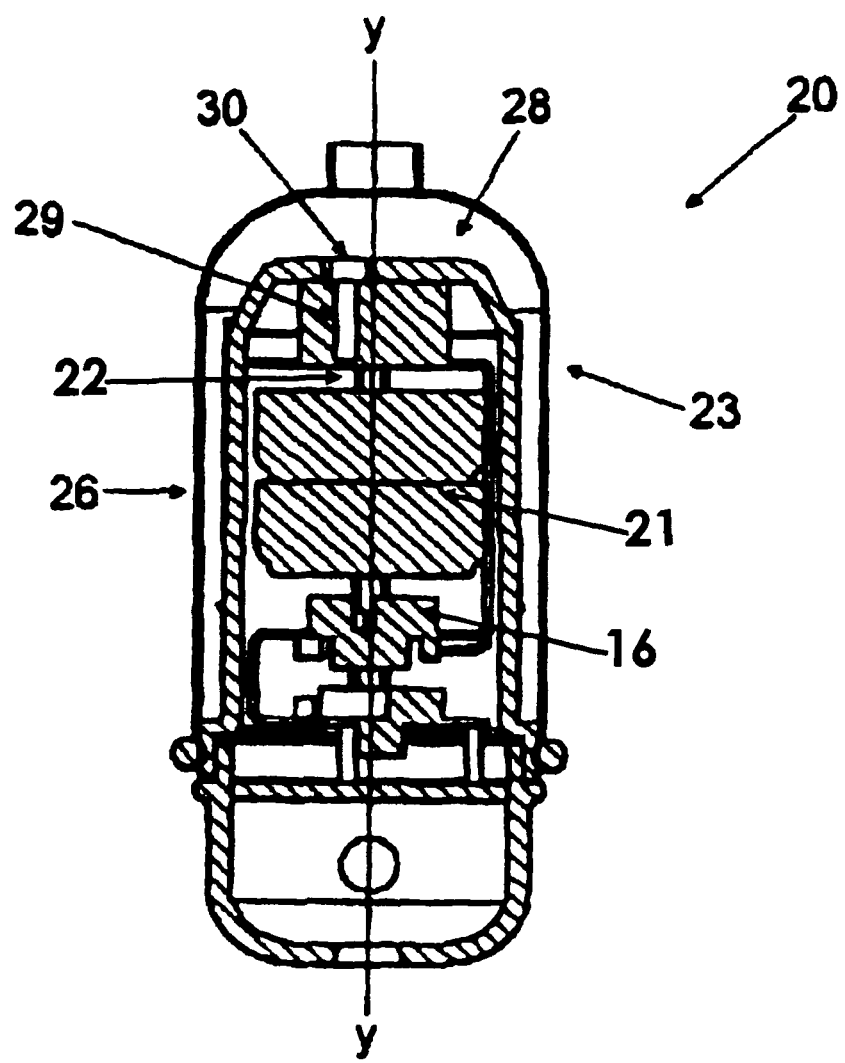
FIG. 11 is a sectional view of an ingestible capsule adapted to record pressure and temperature measurements in a gastrointestinal tract.

As shown in FIG. 11, capsule 20 is generally a cylindrical member elongated about axis y-y and having generally rounded closed ends, somewhat resembling a medicament capsule. The capsule generally has a hard shell or casing which houses the transmitting electronics, a battery compartment, power supply 21, transmitter 16, an antenna, an activation switch, pressure sensor assembly 23, temperature sensor 22 and capacitor 24. Capsule 20 is adapted to be ingested or otherwise positioned within a tract to sense both pressure and temperature within the tract and to transmit such readings to receiver 17. The capsule is generally provided with an outer surface to facilitate easy swallowing of the capsule. In this embodiment, capsule 20 is an autonomous swallowable capsule and is self-contained. Thus, capsule 20 does not require any wires or cables to, for example, receive power or transmit information. The pressure and/or temperature data is transmitted from capsule 20 within the gastrointestinal tract to a remote data receiver 17.

Pressure sensor assembly 23 comprises a flexible sleeve 26 affixed to the shell of the capsule and defining a chamber 28 between the shell and the sleeve. Chamber 28 is filled with a fluid, which is a non-compressible medium that transfers a force acting upon sleeve 26 to sensing mechanism 29 of sensor 23. In this embodiment, the fluid used is a dielectric gel. Alternatively, it is contemplated that other fluids, such as mineral oil, or an inert gas may be used. Sensor 29 is operatively arranged to communicate with chamber 28 through fluid port 30 at one end of the shell of the capsule. As shown in FIG. 11, pressure sleeve 26 of capsule 20 extends from a point below the middle of the capsule up over the top end of the capsule. Thus, pressure sensor 29 is operatively arranged to sense pressure within chamber 28. An analog to digital converter is provided to convert the analog signal from sensor 29 to a digital signal.

In this embodiment, power supply 21 is a silver-oxide battery, although it is contemplated that other batteries may be used, such as a lithium battery. Power supply 21 is adapted to power the electrical components of capsule 20 when in the gastrointestinal tract of a subject.

Capsule 20 is ingested by a subject. Readings are then taken from sensors 22, 23, and 24 on capsule 30 as the capsule passes through at least the end of portion of the gastrointestinal tract of the subject. Data from temperature sensor 22, pressure sensor 23, and capacitor 24 is transmitted from transmitter 16 to data receiver 17. Receiver 17 is generally worn on the belt of the subject and contains rechargeable batteries as its power source. Data receiver 17 records the transmitted data while the capsule passes through the subject's body. After data recording is complete, the data receiver is placed into a docking station. The docking station is connected to computer 19 through a USB connection. The docking station will recharge data receiver 17's batteries and will transfer the recorded data from data receiver 17 to computer 19. In this embodiment, computer 19 is a conventional laptop or desktop computer.

Once the data is downloaded to computer 19, it is analyzed and used in determining the body exit time (BET) of capsule 20 from the subject. The computer workstation also uses the data to calculate several measures of confidence in the body exit time determination, which are used to make a determination if the BET calculation should be used or not 52.

In this embodiment, computer 19 includes a processor 31, data processing storage 34, a monitor or display 32 and a user input device 33. In this embodiment, monitor 32 is a computer screen. However, monitor 32 may be any other device capable of displaying an image or other data. In the preferred embodiment, user input device 33 includes a keyboard and a mouse. However, user input device 33 could be any other suitable input-output device for interfacing with data processor 31.

The processing and analysis of the pressure, temperature, and voltage measurements from capsule 20 is generally provided using computer-executable instructions executed by a general-purpose computer, such as a server or personal computer 19. However, it should be noted that this processing and analysis may be practiced with other computer system configurations, including internet appliances, hand-held devices, wearable computers, multi-processor systems, programmable consumer electronics, network PCs, mainframe computers and the like. The term computer or processor as used herein refers to any of the above devices as well as any other data processor. Some examples of processors are microprocessors, microcontrollers, CPUs, PICs, PLCs, PCs or microcomputers. A computer-readable medium comprises a medium configured to store or transport computer readable code, or in which computer readable code may be embedded. Some examples of computer-readable media are CD-ROM disks, ROM cards, floppy disks, flash ROMS, RAM, nonvolatile ROM, magnetic tapes, computer hard drives, conventional hard disks, and servers on a network. The computer systems described above are for purposes of example only. An embodiment of the invention may be implemented in any type of computer system or programming or processing environment. In addition, it is meant to encompass processing that is performed in a distributed computing environment, were tasks or modules are performed by more than one processing device or by remote processing devices that are run through a communications network, such as a local area network, a wide area network or the internet. Thus, the term processor is to be interpreted expansively.

Computer 19 is programmed to extract information from the pressure measurements taken by pressure sensor 23, the temperature measurements taken by temperature sensor 22, and the capacitor discharge times for capacitor 24, and to use that data to make a determination regarding the BET of capsule 20 from the subject. The analysis and determination of BET is displayed in graphical form on monitor 32 for the user.

Figure 1B:
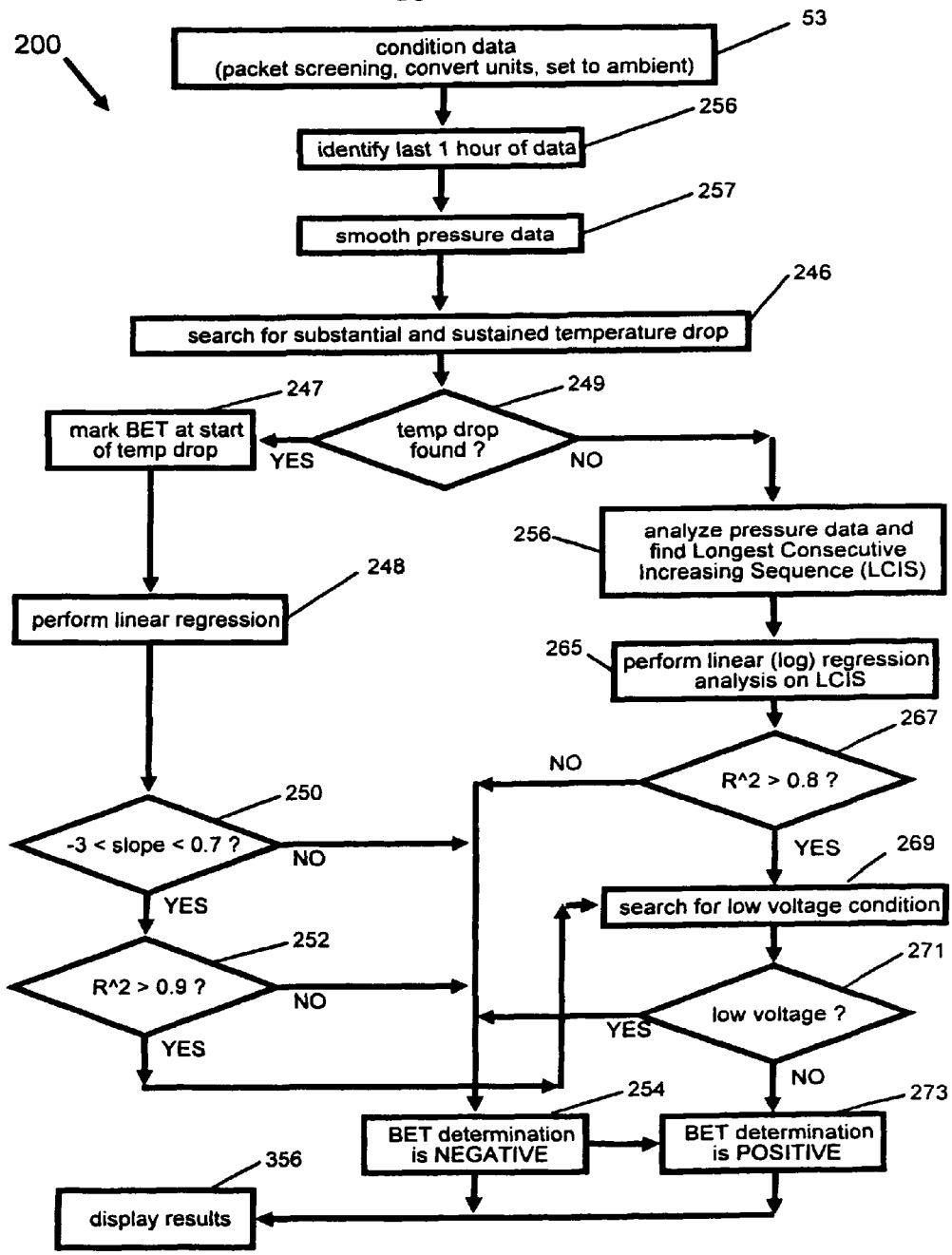
FIG. 1B is a more detailed flow chart of the processing steps shown in FIG. 1A.

Referring now to the flow diagram in FIGS. 1A and 1B, capsule 20 is provided 40 to a subject and is ingested 41 by the subject. Temperature, pressure, and capacitor measurements are recorded 42 by sensors 22 and 23 and capacitor 24. The raw data measurements are then transmitted 43 in data packets to receiver 17, which is outside the gastrointestinal tract of the subject. After the recording period is complete, the receiver is then seated in a docking station connected to computer 19 through a USB connection which then transfers 44 the raw data from receiver 17 to computer 19.

Next, the data is analyzed 200 by computer 19 and used to make a determination of whether the BET of capsule 20 can be established and, if so, the BET. This determination is a function of a number of different variables.

First, the raw data measurements are conditioned 53 by computer 19 through the removal of invalid packets, conversion of the data into proper units and the scaling of pressure to ambient. The invalid packets are screened using a conventional packet validation process. Next, the temperature and pressure measurements are respectively converted into units of degrees Celsius and millimeters of mercury. With respect to the capacitance measurements, capacitor 24 charges and discharges and the discharge times of capacitor 24 are recorded and transmitted within each data packet. The timing is then converted into a voltage reading. In this embodiment, power source voltage is calculated as 0.0195 multiplied by the discharge time less 2.0513. The constant 0.0195 is the voltage count portion and the constant 2.0513 is the voltage offset for this embodiment.

Figure 2:
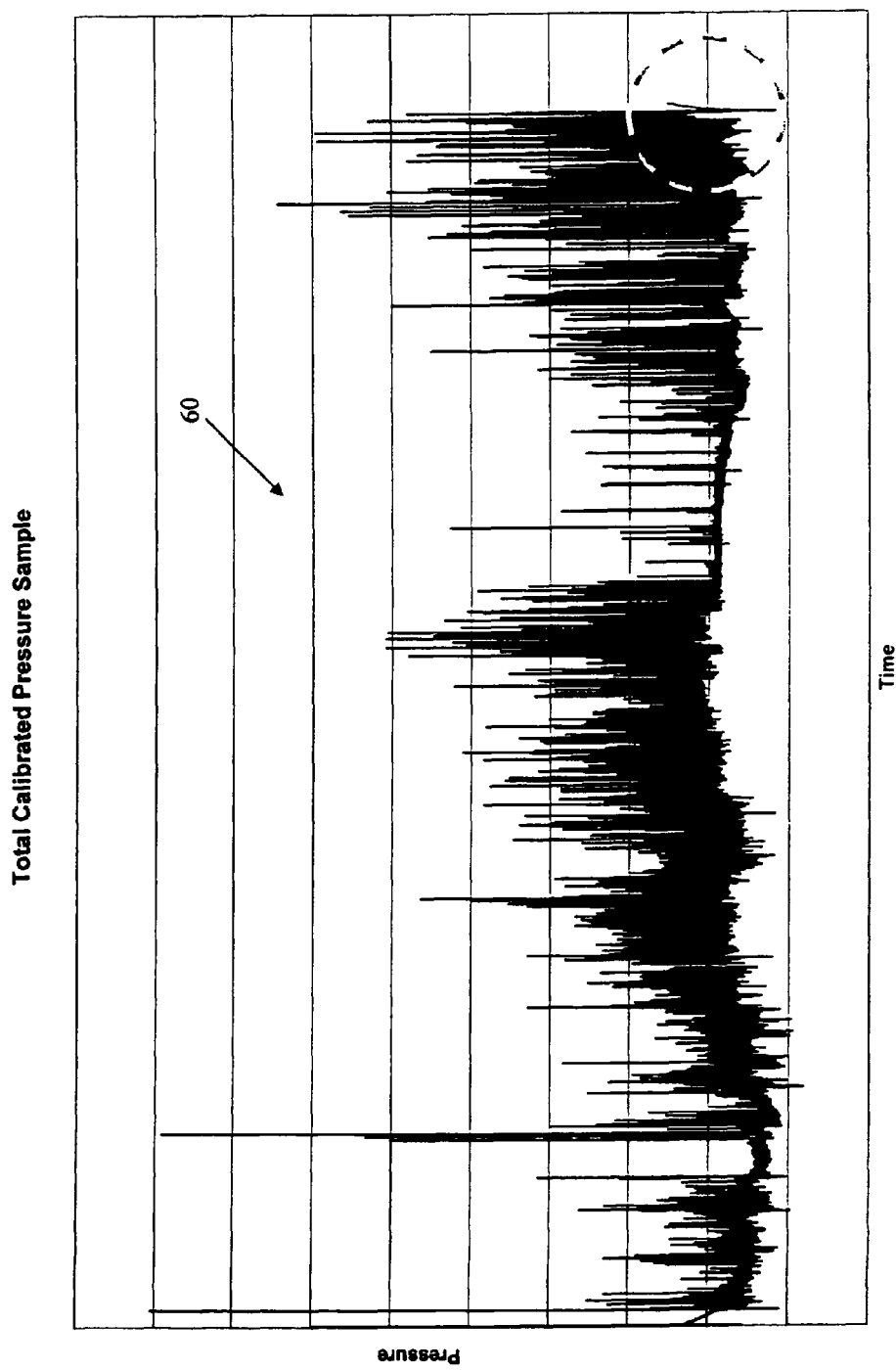
FIG. 2 is a graph of pressure versus time taken by a capsule passing through the gastrointestinal tract of a subject.
Figure 3:
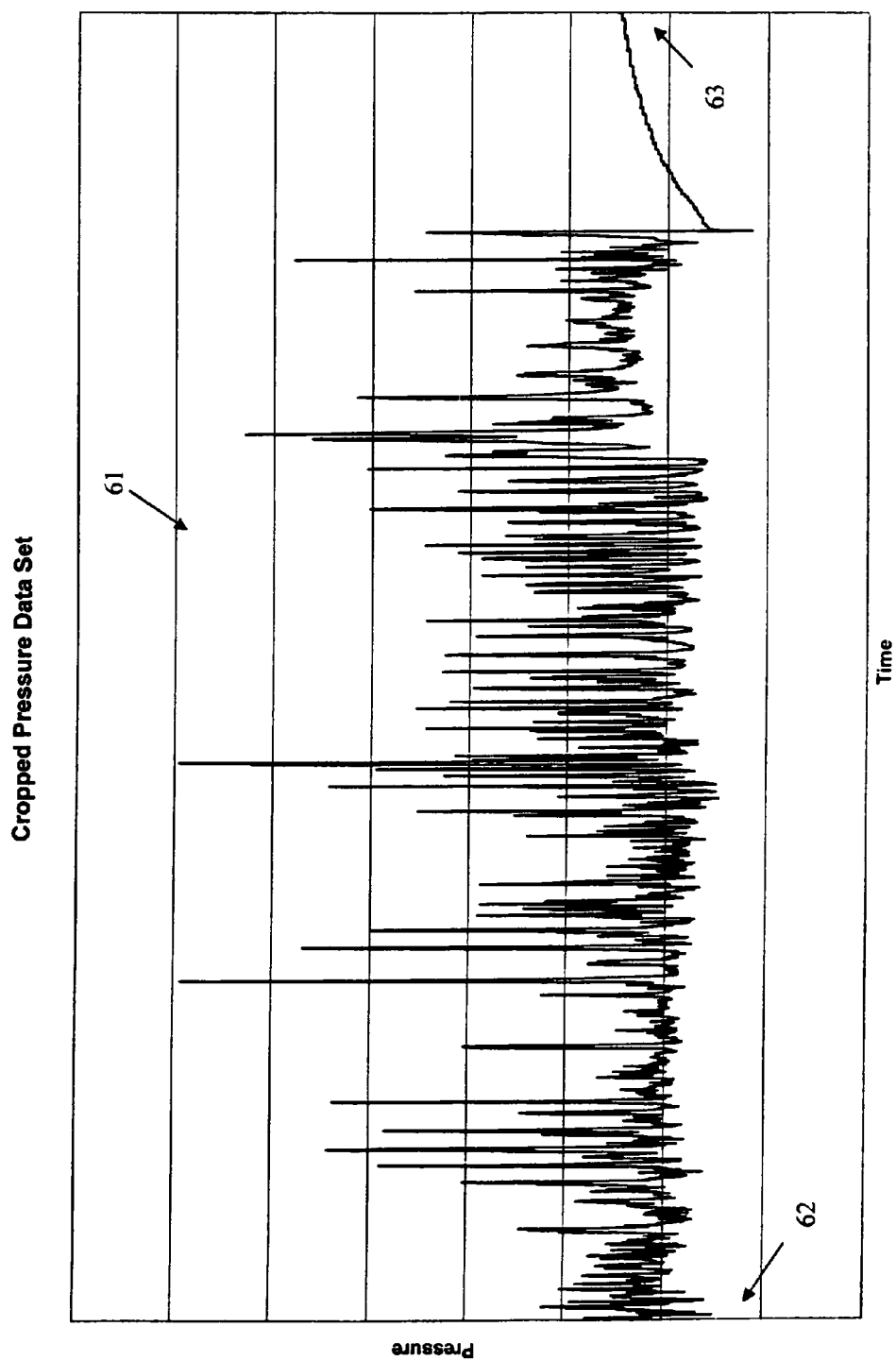
FIG. 3 is a graph of pressure for the period of time shown within the indicated area of FIG. 2.

Next, computer 19 is programmed to identify 256 the last hour of data received from capsule 20 by receiver 17. As shown in FIG. 2, the last recorded transmission is labeled as analysis end time 63, and the time one hour prior to analysis end time 63 is labeled as analysis start time 62. FIG. 3 shows the cropped pressure data between the determined analysis start time 62 and analysis end time 63. While in this embodiment, analysis end time 63 is defined as the transmission end time, it is contemplated that analysis end time 63 may be based on other parameters, such as an event that is recorded by the subject, elapsed time after ingestion, a particular recorded parameter, or a time otherwise identified by the user.

Figure 4:
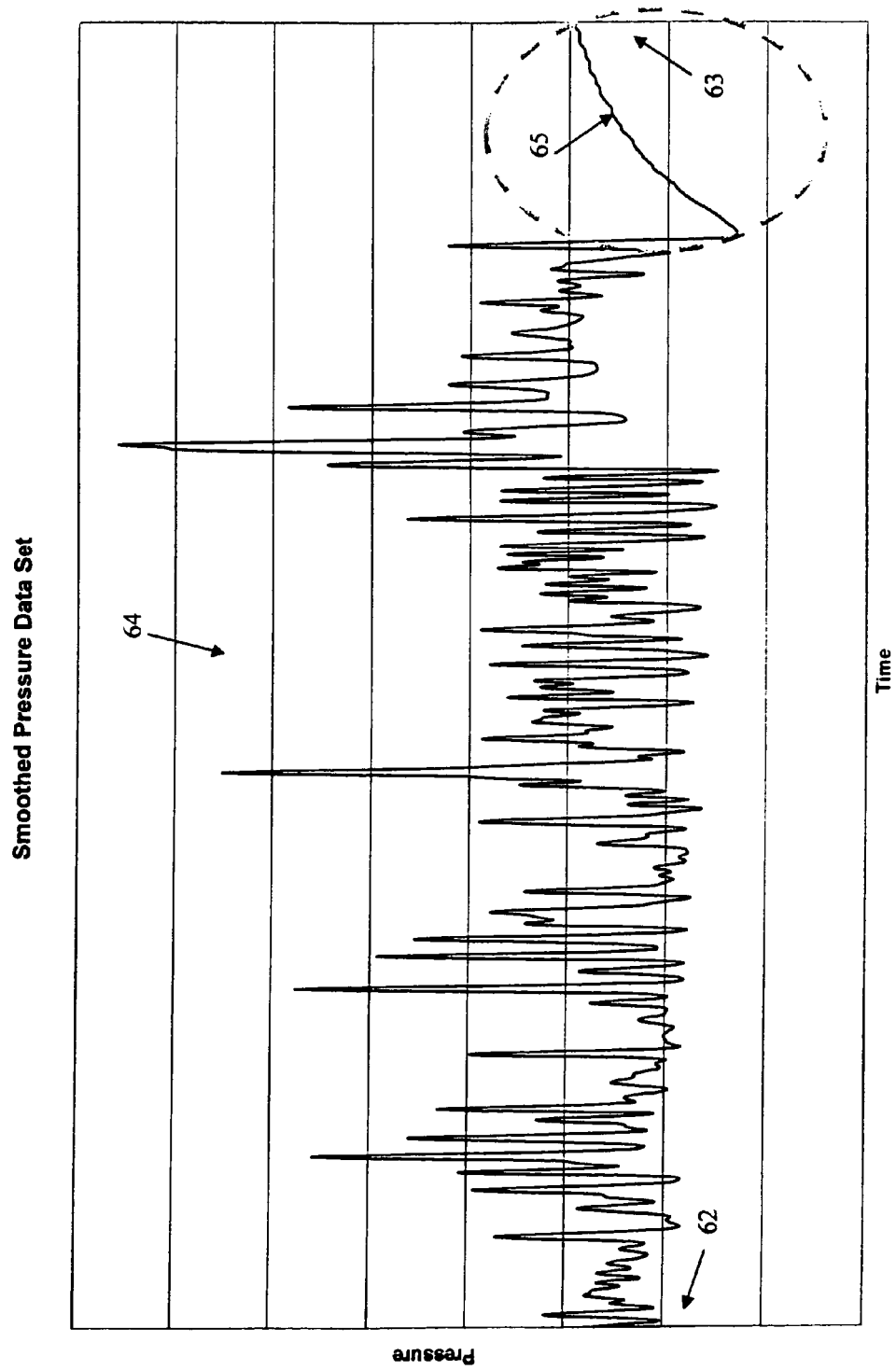
FIG. 4 is a graph of the conditioned pressure measurements for the period of time shown in FIG. 3.
Figure 5:
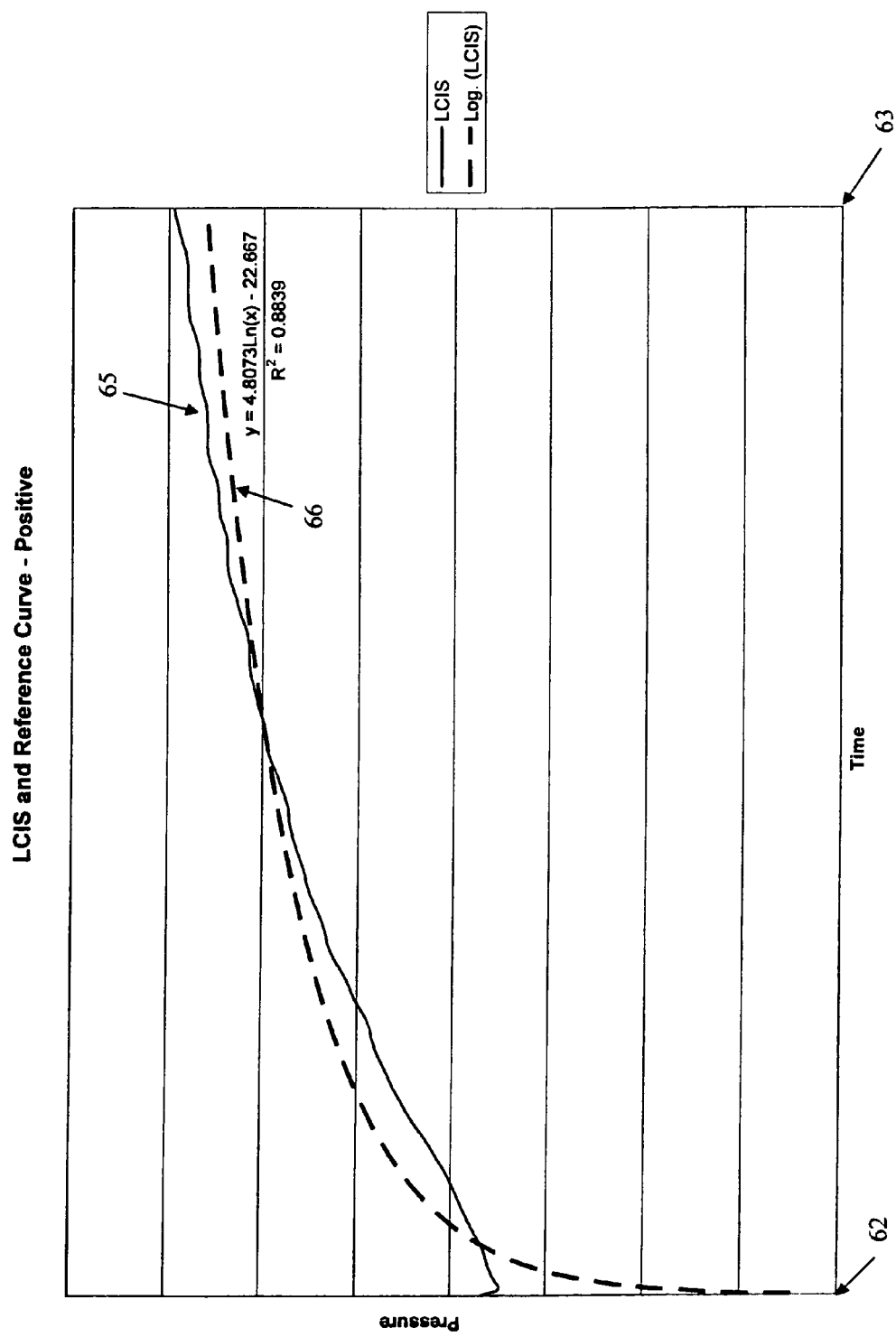
FIG. 5 is a graph of the increasing pressure sequence shown within the indicated area of FIG. 4 together with a logarithmic regression best fit curve with a positive correlation.

Signal filtering 257 of the pressure data with a moving average is then applied to smooth the cropped pressure data. In particular, in this embodiment a window of the five values on each side of each element in the data array is averaged together and this average value placed into a new array of smoothed values. This process is continued until all elements in the original array have been the center of a window. This smoothing is repeated three times to try to eliminate variations which might adversely impact the finding of the longest consecutive increasing sequence (LCIS) in pressure. While this smoothed data is used to determine the LCIS in pressure, it should be understood that the regressions discussed below may be applied to the unsmoothed data set after the LCIS in pressure has been determined. FIG. 4 shows the pressure data from FIG. 3 after smoothing.

Figure 7:
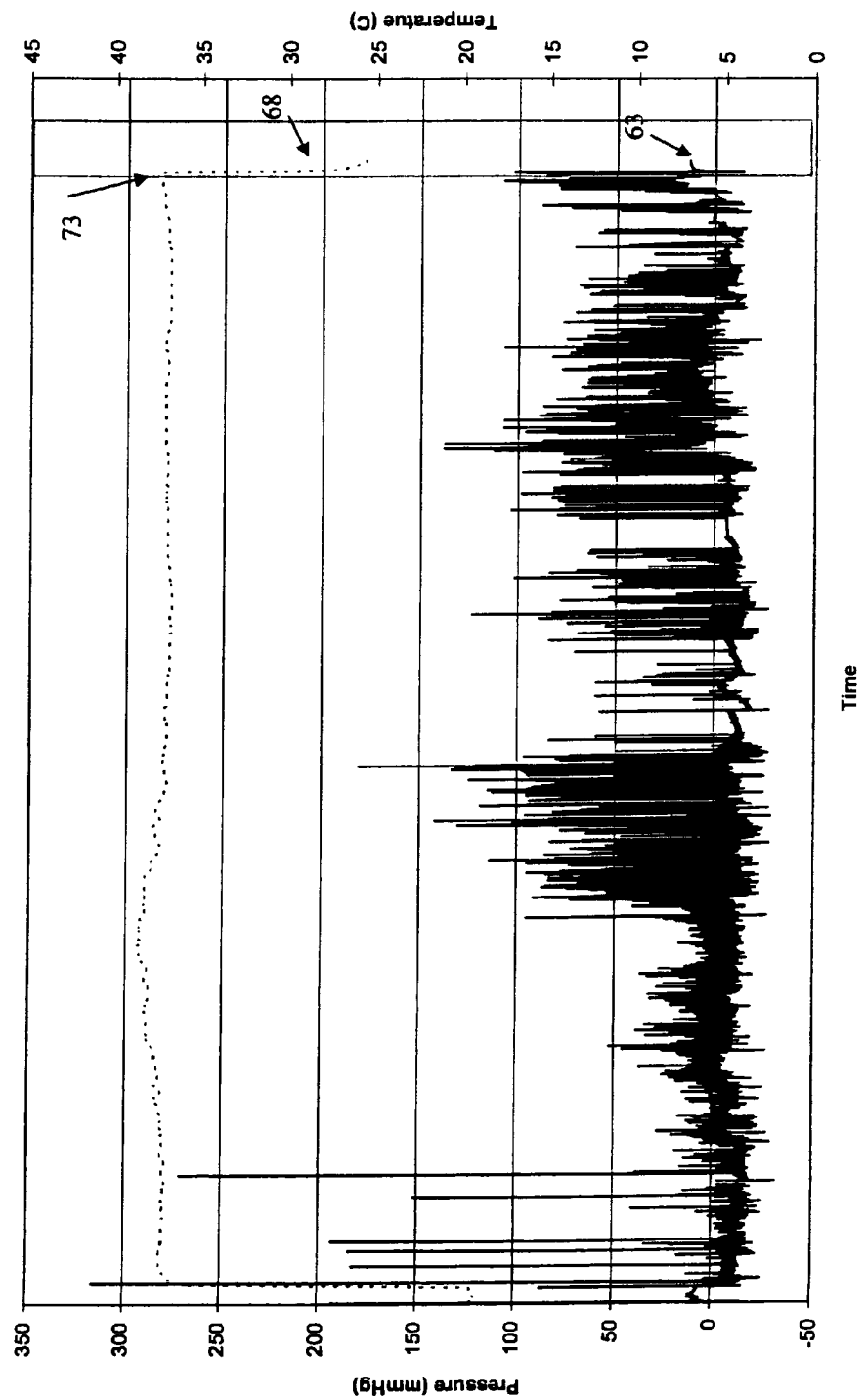
FIG. 7 is a graph of both pressure and temperature versus time taken by a capsule passing through the gastrointestinal tract.

The program then searches 246 the conditioned temperature measurements between analysis begin time 62 and analysis end time 63 for a substantial and sustained temperature drop 68, as shown in FIG. 7. If a substantial temperature drop 68 is identified 249 by this analysis 46, the beginning 73 of that temperature drop is initially marked 247 as the BET. The beginning 73 of the drop in temperature 68 is identified by determining the average temperature for all of the temperature data and then searching backwards through the temperature data for the first temperature sample that is at least 1° C. less than the average. A substantial temperature drop is positively identified if such a drop in temperature of 1° C. or greater from the average is identified in the subject temperature measurements. However, if no substantial temperature drop is identified 249, the program then analyzes 263 the pressure measurements in an attempt to determine the BET.

Unexpectedly, a certain pattern or sequence of increasing pressure 65 in the test data can be used to indicate the BET of capsule 20. In particular, computer 19 is programmed to identify 47 the LCIS sequence 65 in the smoothed pressure data between selected analysis start time 62 and selected analysis end time 63. The identified longest consecutive increasing pressure sequence 65 is characterized in this embodiment by a gradual and sustained increase in calibrated pressure of at least 1.6 mmHg/per minute continuing until the analysis end time (63). This LCIS is then compared to a reference 48.

In this embodiment, computer 19 performs 265 a conventional linear regression analysis on the pressure vs. natural logarithm of time data for the increasing pressure sequence 65. The following conventional linear regression equations are used for the slope and intercept of the best fit line 66, and R2 is the coefficient of determination:

For the longest increasing pressure sequence of N data points $(y_i, t_i)$; $i=1 \ldots N$
where,
  $y_i$=pressure data
  $t_i$=time
  $x_i=\ln(t_i)$
The best fit line is given by $$y = \text{slope}[x] + \text{intercept}$$

where, $$\text{slope} = \frac{N \sum_{i=1}^{N} x_i y_i - \sum_{i=1}^{N} x_i \sum_{i=1}^{N} y_i}{N \sum_{i=1}^{N} x_i^2 - \left(\sum_{i=1}^{N} x_i\right)^2}$$

$$\text{intercept} = \frac{N \sum_{i=1}^{N} x_i y_i - \sum_{i=1}^{N} x_i \sum_{i=1}^{N} y_i}{N \sum_{i=1}^{N} x_i^2 - \left(\sum_{i=1}^{N} x_i\right)^2}$$

and the coefficient of determination is $$R^2 = \frac{\left(N \sum_{i=1}^{N} x_i y_i - \sum_{i=1}^{N} x_i \sum_{i=1}^{N} y_i\right)^2}{\left(N \sum_{i=1}^{N} x_i^2 - \left(\sum_{i=1}^{N} x_i\right)^2\right)\left(N \sum_{i=1}^{N} y_i^2 - \left(\sum_{i=1}^{N} y_i\right)^2\right)}$$

Figure 6:
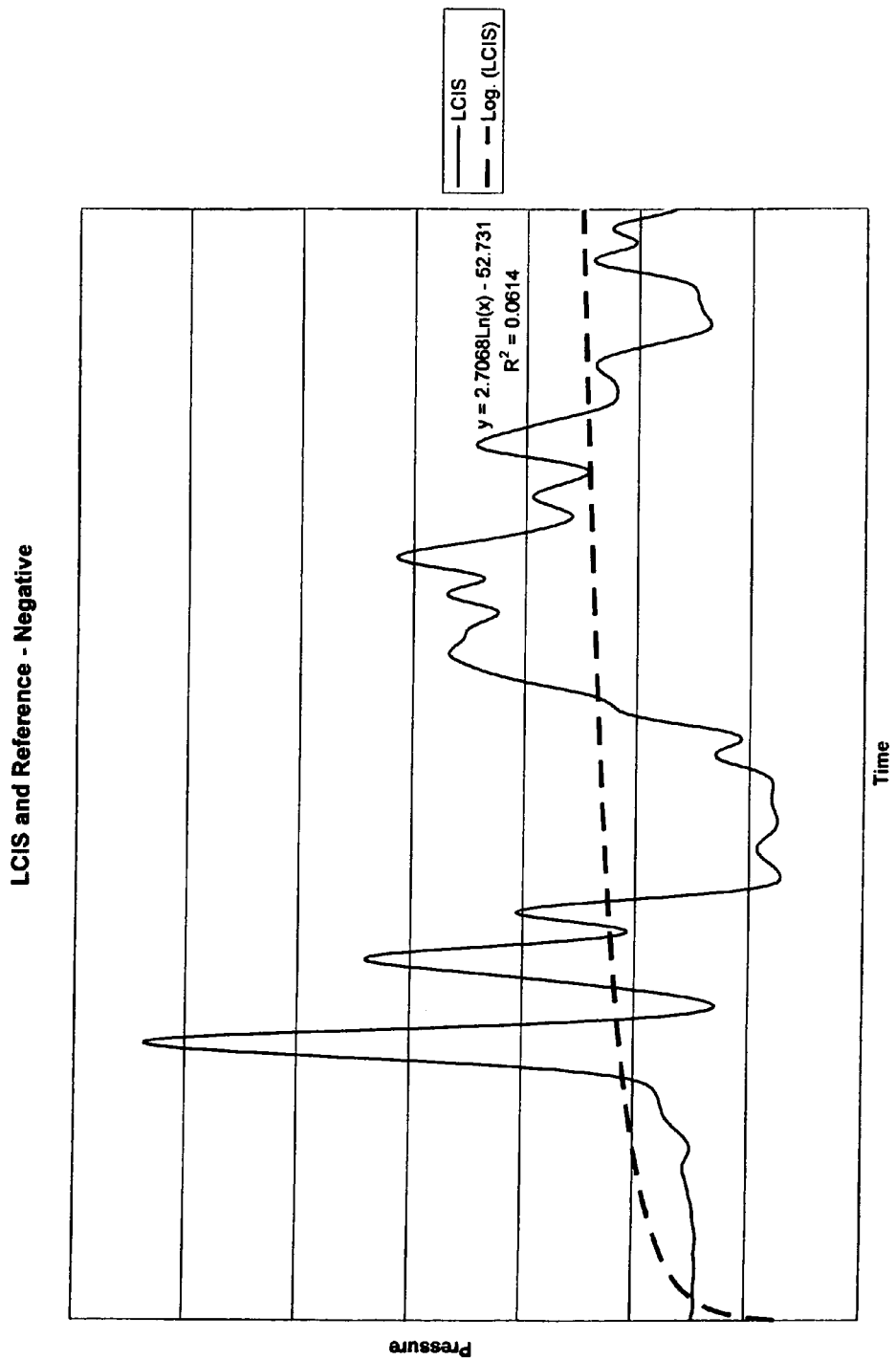
FIG. 6 is a graph of the increasing pressure sequence together with a logarithmic regression best fit curve with a negative correlation.

A high $R^2$ value indicates a strong linear correlation between pressure and ln (time). The calculated $R^2$ is unexpectedly a good indicator of whether the BET occurs at the beginning of the longest continuous increase in pressure. If $R^2$ is about 0.8 or greater, the pressure data is a good indicator of BET, and the start 74 of pressure tail 65 is marked as the BET as shown on FIG. 4. Alternatively, if the coefficient of determination is less than about 0.8, as shown in FIG. 6, then the pressure data is not used to determine BET.

In addition, the voltage data is used to evaluate 45 whether the BET determination is valid or not. Computer 19 is programmed to analyze the voltage measurements for a low voltage condition 269. In the preferred embodiment, a low voltage condition is indicated when a series of decreasing voltage measurements over a time period are identified. Alternatively, the low voltage condition may be indicated when one or more voltage measurements are less than about 2.5 volts. However, the low voltage condition will depend on the particular circuitry of capsule 20. A low voltage condition indicates a negative determination 273 regarding BET, as the pressure and temperature measurements are suspect. On the other hand, if a low voltage condition is not indicated and pressure tail 65 is identified that matches logarithmic curve 66 with a coefficient of determination ($R^2$) of about 0.8 or greater, then a positive determination 254 for BET is marked, whether or not a drop in temperature 68 has been identified in temperature data 249.

Computer 19 is programmed to provide other confirming or non-confirming variables for determining BET. As described above, computer 19 is programmed to search for a substantial drop in the temperature data 246 in the last hour of data 62 to 63. If a substantial temperature drop has been identified 249 the computer 19 will then mark 247 the BET at the beginning of the temperature drop 73.

Figure 8:
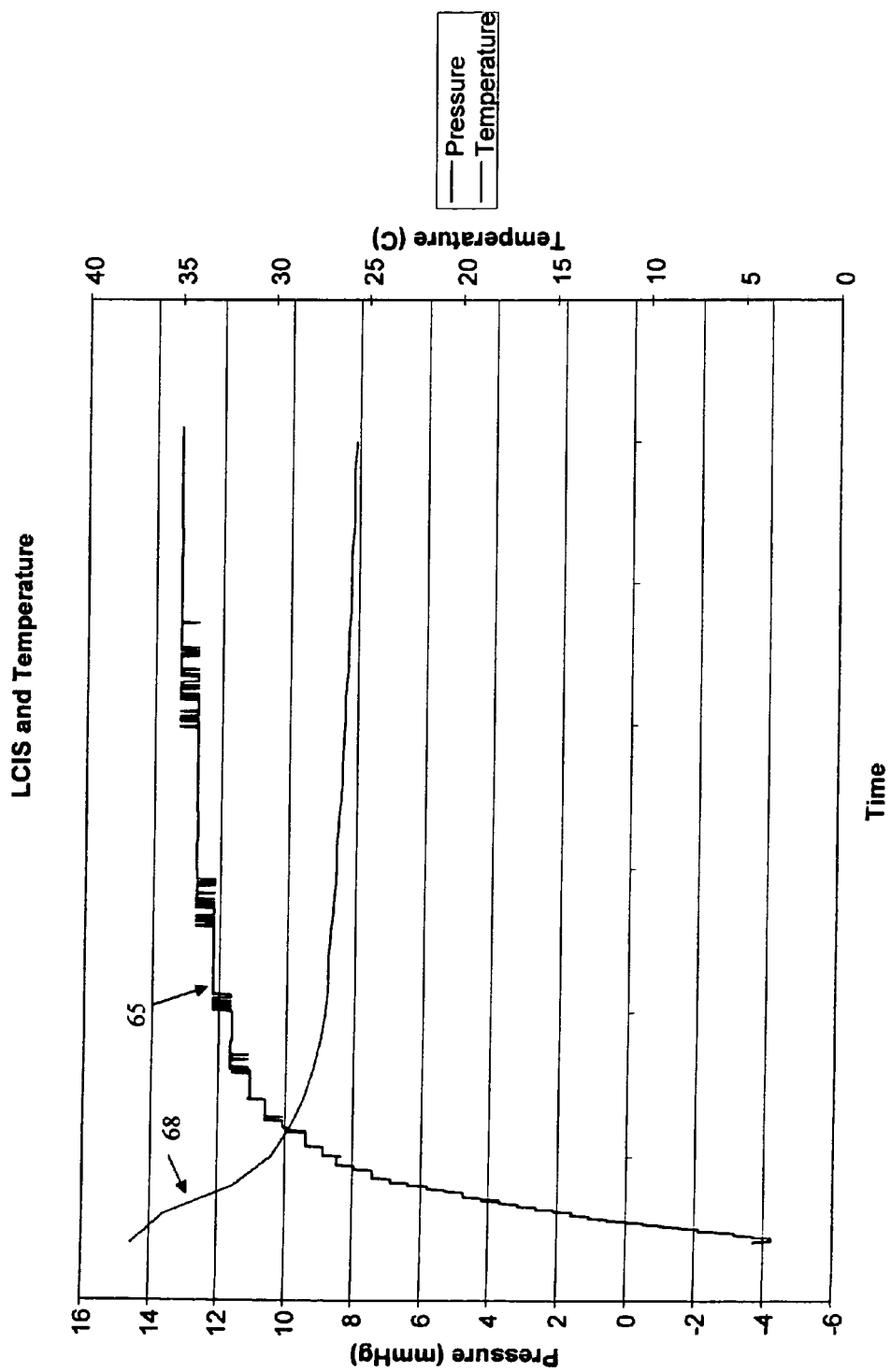
FIG. 8 is a graph of pressure and temperature versus time shown within the indicated area of FIG. 7.

Computer 19 analyzes the relationship 51 between the conditioned temperature and pressure data 51 and compares 57 such relationship to a reference and determines a correlation value 50 for the data. In this embodiment, the program provides a terminating data set 49 of pressure and temperature measurements 69, which is essentially a plot of temperature verses pressure between the beginning 73 of the drop in temperature 68 and the end 63 of pressure tail 65, as shown in FIG. 8.

The program then performs a conventional linear regression analysis 249 of the pressure and temperature measurements in the terminating data set 49. The following conventional linear regression equations are used for the slope and intercept of the best fit line 66, and R2 is the coefficient of determination:

For the sequence of N data points $(y_i, x_i)$; $i=1 \ldots N$
where,
  $y_i$=pressure data
  $x_i$=temperature data
The best fit line is given by $$y = \text{slope}[x] + \text{intercept}$$

where, $$\text{slope} = \frac{N \sum_{i=1}^{N} x_i y_i - \sum_{i=1}^{N} x_i \sum_{i=1}^{N} y_i}{N \sum_{i=1}^{N} x_i^2 - \left(\sum_{i=1}^{N} x_i\right)^2}$$

$$\text{intercept} = \frac{N \sum_{i=1}^{N} x_i y_i - \sum_{i=1}^{N} x_i \sum_{i=1}^{N} y_i}{N \sum_{i=1}^{N} x_i^2 - \left(\sum_{i=1}^{N} x_i\right)^2}$$

and the coefficient of determination is $$R^2 = \frac{\left(N \sum_{i=1}^{N} x_i y_i - \sum_{i=1}^{N} x_i \sum_{i=1}^{N} y_i\right)^2}{\left(N \sum_{i=1}^{N} x_i^2 - \left(\sum_{i=1}^{N} x_i\right)^2\right)\left(N \sum_{i=1}^{N} y_i^2 - \left(\sum_{i=1}^{N} y_i\right)^2\right)}$$

Figure 9:
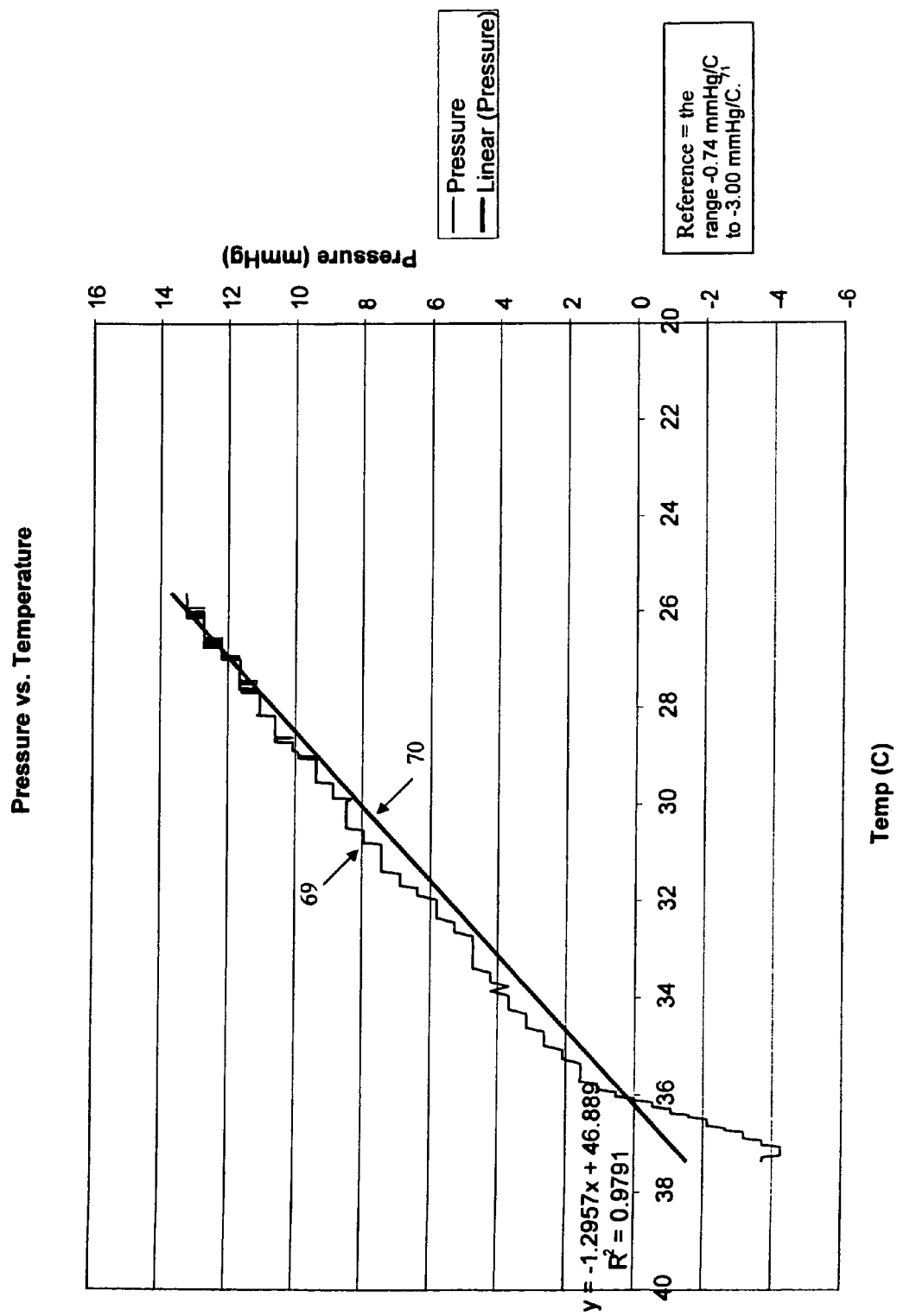
FIG. 9 is a graph of pressure plotted against temperature in ordered pairs for the time shown in FIG. 8 together with a linear regression best fit line.

FIG. 9 is a plot of the pressure vs. temperature curve 69 from temperature drop point 73 to analysis end point 63. The calculated slope of the best fit line is then checked 250 to see if it is within a target range. In this embodiment, the target range is set to the expected thermal coefficient of sensitivity for pressure sensor 23. The thermal coefficient of sensitivity is a predetermined measure of how the pressure sensor measurement is expected to vary with temperature. In the preferred embodiment, the thermal coefficient of sensitivity of pressure sensor 23 is about −0.7 to about −3 mmHg/C. If the slope of line 70 does not fall within the target range, it will indicate a negative determination 254 for BET with respect to this variable. If the slope of best fit line 70 falls within the range of about −0.7 to about −3, it indicates a positive determination for BET with respect to the slope of the best fit line and the program will next analyze the $R^2$ of the best fit line 252.

In this embodiment, the program determines $R^2$ of best fit line 70. A high $R^2$ value indicates a strong linear correlation between pressure and temperature. The calculated $R^2$ is unexpectedly a good indicator of whether the BET occurs at the beginning of the LCIS in pressure. An $R^2$ of 0.9 or greater indicates that the data is likely to yield a positive estimate of BET, and prompts the computer 19 to check for a low voltage condition 269 in the data as discussed earlier. However, if the $R^2$ correlation coefficient of the linear regression is less than about 0.9, then the analysis indicates a negative determination 254 regarding BET.

After the computer 19 has determined whether the BET calculation is positive 273 or negative 254, the result is displayed 56 on computer monitor 32.

While the above embodiments have been described in relation to the gastrointestinal tract of a human, it is contemplated that the system may be used in connection with the gastrointestinal tract of other animals.

The present invention contemplates that many changes and modifications may be made. Therefore, while the presently-preferred form of the improved method has been shown and described, and a number of alternatives discussed, persons skilled in this art will readily appreciate that various additional changes and modifications may be made without departing from the spirit of the invention, as defined and differentiated by the claims.

What is claimed is:

1. A method of determining body exit of an ingestible capsule comprising the steps of:
   recording measurements from a pressure sensor included in said capsule as said capsule passes through at least an end portion of a gastrointestinal tract of said subject; and
   transmitting said measurements to a processor outside of said gastrointestinal tract of said subject, said processor configured to;
      identify a sequence of consecutively increasing pressure measurements in said measurements concurrently as the capsule traverses through said end portion of the gastrointestinal tract from a selected start time to a transmission end time;
      compare said sequence to a reference; and
      determine said capsule exiting said gastrointestinal tract of said subject based on said comparison.

2. The method set forth in claim 1, wherein said increasing pressure sequence is the longest increasing pressure sequence in said measurements.

3. The method set forth in claim 1, wherein said reference is a logarithmic regression of said measurements.

4. The method set forth in claim 1, wherein said ingestible capsule further comprises a temperature sensor.

5. The method set forth in claim 4, and further comprising the steps of:
   recording measurements from said temperature sensor as said capsule passes through said end portion of said gastrointestinal tract of said subject; and
   transmitting said measurements to said processor, said processor further programmed to;
      analyze said temperature measurements for a drop in said temperature measurements; and
      determine said capsule exiting said gastrointestinal tract of said subject also based on said analysis of said temperature measurements.

6. The method set forth in claim 1, further comprising the step of conditioning said measurements between said selected start time and said transmission end time to provide terminating pressure data as a function of time, and wherein said increasing pressure sequence is identified in said terminating pressure data.

7. The method set forth in claim 6, wherein said step of conditioning said measurements comprises the steps of:
   screening said measurements to verify that they are valid;
   converting said measurements to units of pressure; and
   scaling said units of pressure such that ambient atmospheric pressure is set at a zero baseline.

8. The method set forth in claim 1, wherein said step of transmitting said measurements to a processor comprises the steps of:
   transmitting said measurements from said capsule to a receiver outside of said gastrointestinal tract of said subject; and
   downloading said measurements from said receiver to said processor.

9. The method set forth in claim 1, wherein said selected start time is one hour prior to said transmission end time.

10. The method set forth in claim 1, further comprising the step of providing a positive determination regarding said capsule exiting said gastrointestinal tract of said subject when said comparison indicates a match.

11. The method set forth in claim 10, wherein a standard correlation coefficient of 0.8 or greater indicates that said comparison is a match and a standard correlation coefficient of less than 0.8 indicates that said comparison is not a match.

12. The method set forth in claim 5, further comprising the step of providing a positive determination regarding said capsule exiting said gastrointestinal tract of said subject when said comparison indicates a match or there is said drop in said temperature measurements.

13. The method set forth in claim 5, further comprising the step of providing a negative determination regarding said capsule exiting said gastrointestinal tract when said comparison indicates not a match and there is not said drop in said temperature measurements.

14. The method set forth in claim 1, wherein said ingestible capsule further comprises a power source adapted to provide current to an electrical circuit housed in said capsule.

15. The method set forth in claim 14, and further comprising the steps of:
   measuring voltage for said circuit as said capsule passes through said gastrointestinal tract of said subject; and
   transmitting said voltage measurements to said processor, said processor further programmed to;
      analyze said voltage measurements for a low voltage condition; and
      determine said capsule exiting said gastrointestinal tract of said subject based on said analysis of said voltage measurements.

16. The method set forth in claim 15, and further comprising the step of providing a negative determination regarding said capsule exiting said gastrointestinal tract when said low voltage condition is indicated.

17. The method set forth in claim 16, wherein said low voltage condition comprises a voltage measurement of less than 2.5 volts.

18. The method set forth in claim 16, wherein said low voltage condition comprises a series of decreasing voltage measurements over a time period.

19. The method set forth in claim 1, further comprising the step of displaying said determination on a display.

20. A method of determining body exit of an ingestible capsule comprising the steps of:
- recording measurements from a pressure sensor and a temperature sensor included in said capsule as said capsule passes through at least an end portion of a gastrointestinal tract of said subject;
- measuring voltage for a power source adapted to provide current to an electrical circuit included in said capsule as said capsule passes through said gastrointestinal tract of said subject; and
- transmitting said measurements to a processor outside of said gastrointestinal tract of said subject, said processor programmed to perform the steps of:
  - analyzing said voltage measurements for a low voltage condition;
  - analyzing said temperature measurements for a drop in said temperature measurements;
  - identifying a longest consecutive sequence of increasing pressure measurements in said measurements concurrently as the capsule traverses through said end portion of the gastrointestinal tract from a selected start time to a transmission end time to provide terminating pressure data as a function of time;
  - comparing said sequence to a reference; and
  - making a determination regarding said capsule exiting said gastrointestinal tract of said subject as a function of said comparison, said analysis of said temperature measurements, and said analysis of said voltage measurements.

21. The method set forth in claim 20, wherein said step of making a determination regarding said capsule exiting said gastrointestinal tract of said subject comprises the steps of:
- determining if said comparison is a match;
- determining if there is a corresponding drop in said temperature measurements; and
- determining if there is a low voltage condition.

22. The method set forth in claim 21, further comprising the step of providing a positive determination regarding said capsule exiting said gastrointestinal tract when said comparison is a match, when there is said corresponding drop in said temperature measurements, and when there is not said low voltage condition.

23. The method set forth in claim 21, further comprising the step of providing a negative determination regarding said capsule exiting said gastrointestinal tract when said comparison is not a match, when there is not said corresponding drop in said temperature measurements, and when there is said low voltage condition.

24. A method of determining body exit of an ingestible capsule comprising the steps of:
- recording measurements from a pressure sensor and a temperature sensor included in said capsule as said capsule passes through at least an end portion of a gastrointestinal tract of said subject; and
- transmitting said measurements to a processor outside of said gastrointestinal tract of said subject, said processor programmed to perform the steps of:
  - analyzing said temperature measurements for a decrease in temperature;
  - providing a terminating data set for said pressure and temperature measurements between said decrease in temperature and a transmission end time;
  - analyzing said terminating data set to determine a relationship between said pressure and said temperature measurements, wherein said relationship comprises the slope of a linear regression of said terminating data set;
  - comparing said relationship to a reference; and
  - determining said capsule exiting said gastrointestinal tract of said subject based on said comparison.

25. The method set forth in claim 24, wherein said reference comprises a thermal coefficient of sensitivity for said pressure sensor in pressure units per units of temperature.

26. The method set forth in claim 25, wherein said step of analyzing said terminating data set comprises the steps of:
- organizing said pressure and temperature measurements into data pairs; performing a linear regression with respect to said data pairs to provide a best fit line; and
- determining the slope of said best fit line.

27. The method set forth in claim 26, wherein said step of comparing said relationship to a reference comprises comparing said slope to said thermal coefficient of sensitivity for said pressure sensor.

28. The method set forth in claim 27, further comprising the step of providing a positive determination regarding said capsule exiting said gastrointestinal tract of said subject when said comparison is positive.

29. The method set forth in claim 24, further comprising the step of conditioning said pressure measurements prior to said step of providing a terminating data set for said pressure and temperature measurements between said decrease in temperature and said transmission end time.

30. The method set forth in claim 29, wherein said step of conditioning said pressure measurements comprises the steps of:
- screening said pressure measurements to verify that they are valid; converting said pressure measurements to units of pressure; and
- scaling said units of pressure such that ambient atmospheric pressure is set at a zero baseline.

31. The method set forth in claim 24, wherein said step of transmitting said measurements to a processor comprises the steps of:
- transmitting said measurements from said capsule to a receiver outside of said gastrointestinal tract of said subject; and
- downloading said measurements from said receiver to said processor.

32. The method set forth in claim 24, wherein said selected start time is one hour prior to said transmission end time.

33. The method set forth in claim 24, wherein said ingestible capsule further comprises a power source adapted to provide current to an electrical circuit housed in said capsule.

34. The method set forth in claim 33, further comprising the steps of:
- measuring voltage for said circuit as said capsule passes through said gastrointestinal tract of said subject; and
- transmitting said voltage measurements to said processor, said processor further programmed to perform the steps of:
  - analyzing said voltage measurements for a low voltage condition; and
  - determining said capsule exiting said gastrointestinal tract of said subject based on said analysis of said voltage measurements.

35. The method set forth in claim 34, wherein said low voltage condition comprises a series of decreasing voltage measurements over a time period.

36. The method set forth in claim 24, wherein said processor is further programmed to perform the steps of:
- determining a correlation value between temperature and pressure data in said terminating data set; and
- determining said capsule exiting said gastrointestinal tract of said subject based on said correlation value.

37. The method set forth in claim 36, wherein said correlation value is an R-squared correlation coefficient for said linear regression.

38. The method set forth in claim 37, wherein a correlation coefficient of 0.9 or greater indicates that said determination is positive and a correlation coefficient of less than 0.9 indicates that said determination is not positive.

39. A method of determining body exit of an ingestible capsule comprising the steps of:
recording measurements from a pressure sensor and a temperature sensor included in said capsule as said capsule passes through at least an end portion of a gastrointestinal tract of said subject; and
transmitting said measurements to a processor outside of said gastrointestinal tract of said subject, said processor programmed to perform the steps of:
analyzing said temperature measurements for a decrease in temperature;
providing a terminating data set for said pressure and temperature measurements between said decrease in temperature and a transmission end time;
determining a correlation value between temperature and pressure data in said terminating data set; and
determining said capsule exiting said gastrointestinal tract of said subject based on said correlation value.

40. The method set forth in claim 39, wherein said step of determining a correlation value between temperature and pressure data in said terminating data set comprises the step of performing a linear regression with respect to said data set.

41. The method set forth in claim 40, wherein said correlation value is an R-squared correlation coefficient for said linear regression.

42. The method set forth in claim 41, wherein a correlation coefficient of 0.9 or greater indicates that said determination is positive and a correlation coefficient of less than 0.9 indicates that said determination is not positive.

43. A non-transitory computer-readable medium having computer-executable instructions for performing a method comprising:
receiving pressure measurements recorded by a pressure sensor on an ingestible capsule ingested by a subject; and
instructing a processor to perform steps comprising:
identifying a sequence of consecutively increasing pressure measurements in said measurements concurrently as the capsule traverses through said end portion of the gastrointestinal tract from a selected start time to a transmission end time;
comparing said sequence to a reference; and
determining said capsule exiting said gastrointestinal tract of said subject based on said comparison.

44. The medium set forth in claim 43, wherein said increasing pressure sequence is the longest increasing pressure sequence in said measurements.

45. The medium set forth in claim 43, wherein said reference is a logarithmic regression of said measurements.

46. The medium set forth in claim 43, and further comprising:
receiving temperature measurements recorded by a temperature sensor on said ingestible capsule; and
instructing said processor to perform further steps comprising:
analyzing said temperature measurements for a drop in said temperature measurements; and
determining said capsule exiting said gastrointestinal tract of said subject based on said analysis of said temperature measurements.

47. The medium set forth in claim 43, and further comprising conditioning said measurements between said selected start time and said transmission end time to provide terminating pressure data as a function of time, and wherein said increasing pressure sequence is identified in said terminating pressure data.

48. The medium set forth in claim 43, wherein said conditioning said measurements comprises:
screening said measurements to verify that they are valid;
converting said measurements to units of pressure; and
scaling said units of pressure such that ambient atmospheric pressure is set at a zero baseline.

49. The medium set forth in claim 43, wherein said selected start time is one hour prior to said transmission end time.

50. The medium set forth in claim 46, and further comprising the steps of
receiving voltage measurements recorded by said ingestible capsule; and
instructing said processor to perform further steps comprising:
analyzing said voltage measurements for a low voltage condition; and
determining said capsule exiting said gastrointestinal tract of said subject based on said analysis of said voltage measurements.

51. A system for identifying the body exit of an ingestible capsule from a gastrointestinal tract comprising:
an ingestible capsule having a pressure sensor adapted to record pressure data as a function of time as said capsule passes through at least a portion of a subject's gastrointestinal tract;
a receiver adapted to received said data when transmitted from said capsule; a processor adapted to communicate with said receiver; a display in communication with said processor; said processor programmed to:
receive pressure measurements recorded by said pressure sensor;
identify a sequence of consecutively increasing pressure measurements in said measurements concurrently as the capsule traverses through said end portion of the gastrointestinal tract from a selected start time to a transmission end time;
compare said sequence to a reference; and
determine said capsule exiting said gastrointestinal tract of said subject based on said comparison.

52. The system set forth in claim 51, wherein said increasing pressure sequence is the longest increasing pressure sequence in said measurements.

53. The system set forth in claim 51, wherein said reference is a logarithmic regression of said measurements.

54. The system set forth in claim 51, wherein:
said ingestible capsule further comprises a temperature sensor adapted to record temperature data as a function of time as said capsule passes through at least a portion of a subject's gastrointestinal tract; and
said processor is further programmed to
receive temperature measurements recorded by said temperature sensor;
analyze said temperature measurements for a drop in said temperature measurements; and
determine said capsule exiting said gastrointestinal tract of said subject based on said analysis of said temperature measurements.

55. The system set forth in claim 51, wherein said processor is further programmed to condition said measurements between said selected start time and said transmission end time to provide terminating pressure data as a function of time, and wherein said increasing pressure sequence is identified in said terminating pressure data.

56. The system set forth in claim 55, wherein, for conditioning said measurements, said processor is further configured to:
screen said measurements to verify that they are valid;
convert said measurements to units of pressure; and
scale said units of pressure such that ambient atmospheric pressure is set at a zero baseline.

57. The system set forth in claim 51, wherein said selected start time is one hour prior to said transmission end time.

58. The system set forth in claim 54, wherein said processor is further programmed to:
receive voltage measurements recorded by said ingestible capsule; and
analyze said voltage measurements for a low voltage condition; and use said analysis of said voltage measurements to make said determination regarding said capsule exiting said gastrointestinal tract of said subject.

59. A non-transitory computer-readable medium having computer-executable instructions for performing a method comprising:
receiving pressure measurements recorded by a pressure sensor and temperature measurements recorded by a temperature sensor on an ingestible capsule ingested by a subject; and
instructing a processor to perform steps comprising:
analyzing said temperature measurements for a decrease in temperature;
providing a terminating data set for said pressure and temperature measurements between said decrease in temperature and a transmission end time;
analyzing said terminating data set to determine a relationship between said pressure and said temperature measurements, where said relationship comprises the slope of a linear regression of said terminating data set;
comparing said relationship to a reference; and
determining said capsule exiting said gastrointestinal tract of said subject based on said comparison.

60. The medium set forth in claim 59, wherein said reference comprises a thermal coefficient of sensitivity for said pressure sensor in pressure units per units of temperature.

61. The medium set forth in claim 59, wherein analyzing said terminating data set comprises:
organizing said pressure and temperature measurements into data pairs; performing a linear regression with respect to said data pairs to provide a best fit line; and
determining the slope of said best fit line.

62. The medium set forth in claim 61, wherein comparing said relationship to a reference comprises comparing said slope to said thermal coefficient of sensitivity for said pressure sensor.

63. The medium set forth in claim 59 and further comprising:
determining a correlation value between temperature and pressure data in said terminating data set; and
determining said capsule exiting said gastrointestinal tract of said subject based on said correlation value.

64. The medium set forth in claim 63, wherein said correlation value is an R-squared correlation coefficient for said linear regression.

65. The medium set forth in claim 64, wherein a correlation coefficient of 0.9 or greater indicates that said determination is positive and a correlation coefficient of less than 0.9 indicates that said determination is not positive.

66. A non-transitory computer-readable medium having computer-executable instructions for performing a method comprising:
receiving pressure measurements recorded by a pressure sensor and temperature measurements recorded by a temperature sensor on an ingestible capsule ingested by a subject; and
instructing a processor to perform steps comprising:
analyzing said temperature measurements for a decrease in temperature;
providing a terminating data set for said pressure and temperature measurements between said decrease in temperature and a transmission end time;
determining a correlation value between temperature and pressure data in said terminating data set; and
determining, said capsule exiting said gastrointestinal tract of said subject based on said correlation value.

67. The medium set forth in claim 66, wherein determining a correlation value between temperature and pressure data in said terminating data set comprises performing a linear regression with respect to said data set.

68. The medium set forth in claim 67, wherein said correlation value is an R-squared correlation coefficient for said linear regression.

69. The medium set forth in claim 68, wherein a correlation coefficient of 0.9 or greater indicates that said determination is positive and a correlation coefficient of less than 0.9 indicates that said determination is not positive.

* * * * *